United States Patent
Jourdan et al.

(10) Patent No.: US 9,754,335 B2
(45) Date of Patent: Sep. 5, 2017

(54) SYSTEM AND METHODS FOR PROVIDING TRANSPORTATION SERVICES IN HEALTH CARE FACILITIES

(71) Applicant: HOSPITAL HOUSEKEEPING SYSTEMS, LLC, Austin, TX (US)

(72) Inventors: Steve Jourdan, Austin, TX (US); Joel Schaubert, Austin, TX (US)

(73) Assignee: HOSPITAL HOUSKEEPING SYSTEMS, LLC, Austin, TX (US)

( * ) Notice: Subject to any disclaimer, the term of this patent is extended or adjusted under 35 U.S.C. 154(b) by 644 days.

(21) Appl. No.: 13/743,943

(22) Filed: Jan. 17, 2013

(65) Prior Publication Data

US 2013/0204633 A1     Aug. 8, 2013

Related U.S. Application Data

(60) Provisional application No. 61/587,502, filed on Jan. 17, 2012.

(51) Int. Cl.
   *G06Q 10/00*    (2012.01)
   *G06Q 50/00*    (2012.01)
   *G06Q 50/22*    (2012.01)
   *G06Q 10/06*    (2012.01)

(52) U.S. Cl.
CPC ....... *G06Q 50/22* (2013.01); *G06Q 10/06311* (2013.01)

(58) Field of Classification Search
CPC ................................ G06Q 50/22; G06Q 50/24
USPC ................................................... 705/2, 3, 4
See application file for complete search history.

(56) References Cited

U.S. PATENT DOCUMENTS

| | | | |
|---|---|---|---|
| 5,699,038 A | 12/1997 | Ulrich et al. | |
| 6,147,592 A | 11/2000 | Ulrich et al. | |
| 6,462,656 B2 | 10/2002 | Ulrich et al. | |
| 6,539,393 B1 | 3/2003 | Kabala | |
| 6,727,818 B1 | 4/2004 | Wildman et al. | |

(Continued)

FOREIGN PATENT DOCUMENTS

WO     03012596 A2    2/2003

OTHER PUBLICATIONS

Ron Gregg "ABCs of Patient Flow" Q2 2007 Future Healthcare, pp. 1-16.

(Continued)

*Primary Examiner* — Michelle L Le
(74) *Attorney, Agent, or Firm* — Meyertons, Hood, Kivlin, Kowert & Goetzel, P.C.

(57) ABSTRACT

A system for providing transportation services in a health care facility includes a communication network, a transportation services management system, one or more dispatcher devices, and one or more transport responder mobile devices. The transportation services management system stores and retrieves information relating to dispatches of transportation services jobs at one or more health care facilities. The dispatch devices exchange, with the transportation services management system, information relating to the transportation services jobs and display information to a transportation dispatch manager. The transport responder mobile devices exchange, with the transportation services management system, information relating to the transportation services jobs and display information to transport responders.

16 Claims, 30 Drawing Sheets

(56) References Cited

U.S. PATENT DOCUMENTS

| | | | |
|---|---|---|---|
| 6,825,763 B2 | 11/2004 | Ulrich et al. | |
| 6,876,303 B2 | 4/2005 | Reeder et al. | |
| 6,897,780 B2 | 5/2005 | Ulrich et al. | |
| 6,954,737 B2 | 10/2005 | Kalantar et al. | |
| 6,983,423 B2 | 1/2006 | Dvorak et al. | |
| 7,015,816 B2 | 3/2006 | Wildman et al. | |
| 7,042,337 B2 | 5/2006 | Borders et al. | |
| 7,092,376 B2 | 8/2006 | Schuman | |
| 7,113,864 B2 | 9/2006 | Smith et al. | |
| 7,237,287 B2 | 7/2007 | Weismiller et al. | |
| 7,242,306 B2 | 7/2007 | Wildman et al. | |
| 7,242,308 B2 | 7/2007 | Ulrich et al. | |
| 7,248,933 B2 | 7/2007 | Wildman | |
| 7,315,535 B2 | 1/2008 | Schuman | |
| 7,319,386 B2 | 1/2008 | Collins, Jr. et al. | |
| 7,408,470 B2 | 8/2008 | Wildman et al. | |
| 7,443,302 B2 | 10/2008 | Reeder et al. | |
| 7,443,303 B2 | 10/2008 | Spear et al. | |
| 7,533,353 B2 | 5/2009 | Dvorak et al. | |
| 7,716,066 B2 | 5/2010 | Rosow et al. | |
| 7,720,695 B2 | 5/2010 | Rosow et al. | |
| 7,734,479 B2 | 6/2010 | Rosow et al. | |
| 7,746,218 B2 | 6/2010 | Collins, Jr. et al. | |
| 7,756,723 B2 | 7/2010 | Rosow et al. | |
| 7,774,215 B2 | 8/2010 | Rosow et al. | |
| 7,796,045 B2 | 9/2010 | Spear et al. | |
| 7,868,740 B2 | 1/2011 | Mcneely et al. | |
| 7,890,347 B2 | 2/2011 | Rosow et al. | |
| 8,005,937 B2 | 8/2011 | Wesley, Sr. et al. | |
| 2003/0204431 A1 | 10/2003 | Ingman | |
| 2006/0143045 A1 | 6/2006 | Nacey | |
| 2006/0247948 A1 | 11/2006 | Ellis et al. | |
| 2007/0067199 A1 | 3/2007 | Shine et al. | |
| 2007/0239484 A1 | 10/2007 | Arond et al. | |
| 2007/0288285 A1* | 12/2007 | Nilsson | 705/9 |
| 2008/0021709 A1 | 1/2008 | Greer | |
| 2008/0027754 A1 | 1/2008 | Auker et al. | |
| 2008/0097804 A1 | 4/2008 | Soltero | |
| 2009/0051526 A1 | 2/2009 | Spear et al. | |
| 2009/0132586 A1* | 5/2009 | Napora et al. | 707/104.1 |
| 2009/0204471 A1 | 8/2009 | Elenbaas et al. | |
| 2009/0254365 A1 | 10/2009 | Gravina | |
| 2009/0313046 A1* | 12/2009 | Badgett et al. | 705/3 |
| 2010/0070294 A1 | 3/2010 | Horne et al. | |
| 2011/0117878 A1* | 5/2011 | Barash et al. | 455/404.2 |
| 2012/0005113 A1 | 1/2012 | Kotis et al. | |

OTHER PUBLICATIONS

"Aionex Effciency and Throughput Suite" 2010 Aionex, pp. 1-10.
"Allina Hospitals and Clinics Selects PatientTrak" PatientTrak Nov. 2010, p. 1.
"Bed Management" 2010, downloaded Jan. 12, 2011 from agiletrac.gehealthcare.com, p. 1.
"El Rio Health Center Successfully Implements PatientTrak Solution" PatientTrak Mar. 2010, p. 1.
"Lakeside Medical Center Successfully Implements PatientTrak Solution" PatientTrak Feb. 2010, p. 1.
"PatientTrak.net" downloaded Jan. 12, 2011 from Patienttrak.net, pp. 1-5.
"Ocean Beach Hospital Implements PatientTrak Solution" PatientTrak Apr. 2010, p. 1.
"TeleTracking—Patient Flow Solutions" 2011 TeleTracking Technologies, Inc, downloaded from teletracking.com on Jan. 12, 2011, pp. 1-18.
"Allscripts—Performance Management Patient Flow" downloaded from allscripts.com on Apr. 13, 2011, pp. 1-9.
"Bed Management" Downloaded from wikipedia.com on Apr. 13, 2011, pp. 1-3.
Computer-Aided Dispatch App Comes to iPhone, iPad Published Feb. 6, 2011 downloaded Sep. 28, 2011 from ems1.com, p. 1.
"Central Logic Edge" 2011, downloaded Sep. 28, 2011 from centrallogic.com pp. 1-2.
"LeFleur Transportation—Trapeze MT" 1999-2011 Trapeze Group Limited. Downloaded Sep. 28, 2011 from trapezegroup.com, pp. 1-2.
"What could "crowd sourcing" a workforce mean to your business?" 2011 Ceridian Corporation. Downloaded Sep. 22, 2011 from ceridian.com, pp. 1-2.
"Crowdsourcing emergency response Pt. 1" Published Jan. 12, 2011 downloaded Sep. 22, 2011 from leagueforhope.org, pp. 1-2.
Amy Every "Best Practices for Controlling Labor Costs" Published Jun. 2008, pp. 1-3.
"Hospitals Try Online Staffing" Published Jan. 13, 2004 downloaded Sep. 22, 2011 from iseek.org, p. 1.
U.S. Appl. No. 61/553,663, filed Oct. 31, 2011, Steve Jourdan et al.
U.S. Appl. No. 13/665,488, filed Oct. 31, 2012, Steve Jourdan et al.
U.S. Appl. No. 13/665,499, filed Oct. 31, 2012, Steve Jourdan et al.
U.S. Appl. No. 13/665,508, filed Oct. 31, 2012, Steve Jourdan et al.
International Serial No. PCT/US2012/062882 filed Oct. 31, 2012, Steve Jourdan et al.
U.S. Appl. No. 61/587,502, filed Jan. 17, 2012, Steve Jourdan et al.
U.S. Appl. No. 13/743,943, filed Jan. 17, 2012, Steve Jourdan et al.
International Serial No. PCT/US13/21884, filed Jan. 17, 2012, Steve Jourdan et al.
U.S. Appl. No. 13/665,488, filed Oct. 31, 2012, Steve Jourdan.
U.S. Appl. No. 13/665,499, filed Oct. 31, 2012, Steve Jourdan.
U.S. Appl. No. 13/665,508, filed Oct. 31, 2012, Steve Jourdan.
International Search Report and Written Opinion in application No. PCT/US2013/021884 mailed Apr. 29, 2013 pp. 1-14.
International Search Report and Written Opinion in application No. PCT/US2012/062882 mailed May 13, 2013 pp. 1-13.
U. S. P.T. O. Non-Final Office Action for U.S. Appl. No. 13/665,488, mailed Jun. 24, 2014.
U. S. P.T. O. Non-Final Office Action for U.S. Appl. No. 13/665,488, mailed Feb. 13, 2015.
U. S. P.T. O. Non-Final Office Action for U.S. Appl. No. 13/665,499, mailed Oct. 1, 2014.
U. S. P.T. O. Non-Final Office Action for U.S. Appl. No. 13/665,508, mailed Feb. 27, 2015.
U. S. P.T. O. Non-Final Office Action for U.S. Appl. No. 13/743,943, mailed Dec. 23, 2014.

* cited by examiner

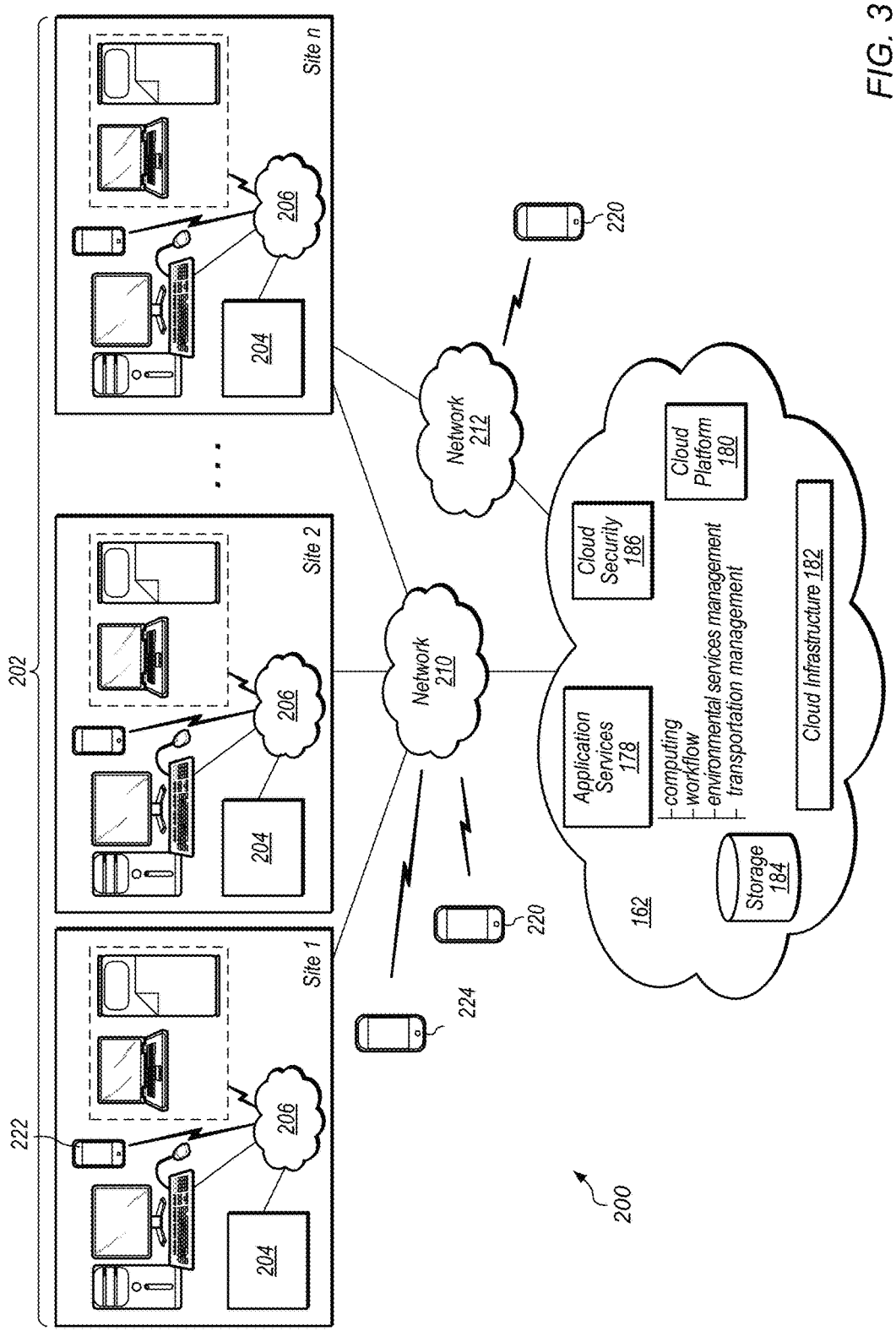

FIG. 4

Acme Hospital ▼ — 242

| | 15% Occupied | Clean: 13 | |
|---|---|---|---|
| | 19 Total Beds | Occupied: 3 | (44 Waiting) |
| | | Dirty: 2 | (1 in progress) |

Page Refresh In: 55  [Reload Now] — 249

— 244

| Unit A | Total: 9 | Clean: 3 | Occupied: 3 | | Waiting: 0 | Dirty: 2 | In Progress: 1 | — 248 |
|---|---|---|---|---|---|---|---|---|
| 1001 | M clean | occupied | dirty | stat | in progress | | | |
| 1002 | F Con. | occupied | dirty | stat | in progress | | | |
| 1003 | M clean | occupied | dirty | stat | in progress | 16 / 0 / 0 min | | — 246 |
| 1004 | clean | occupied | dirty | stat | in progress | | | |
| 1005 | M clean | occupied | dirty | stat | in progress | 15 / 6 / 0 min | | |
| 1006 | F clean | occupied | dirty | stat | in progress | 15 / 0 / 6 min | | |
| 1007 | M clean | occupied | dirty | stat | in progress | Ants in room | | |
| 1008 | clean | occupied | dirty | stat | in progress | | | |
| 1009 | clean | occupied | dirty | stat | in progress | Est Discharge—Mon 4:00 PM | | |
| 1010 | clean | occupied | dirty | stat | in progress | | | |

| Unit B | Total: 10 | Clean: 10 | Occupied: 0 | | Waiting: 0 | Dirty: 0 | In Progress: 0 | |
|---|---|---|---|---|---|---|---|---|
| 2001 | clean | occupied | dirty | stat | in progress | | | |
| 2002 | clean | occupied | dirty | stat | in progress | | | |
| 2003 | clean | occupied | dirty | stat | in progress | | | |
| 2004 | clean | occupied | dirty | stat | in progress | | | |
| 2005 | clean | occupied | dirty | stat | in progress | | | |
| 2007 | clean | occupied | dirty | stat | in progress | | | |
| 2007 | clean | occupied | dirty | stat | in progress | | | |
| 2008 | clean | occupied | dirty | stat | in progress | | | |
| 2009 | clean | occupied | dirty | stat | in progress | | | |
| 2010 | clean | occupied | dirty | stat | in progress | | | |

240

Acme Hospital ▶    12% Occupied    Clean: 15    [Resend Page]

Page Refresh In: 47   [Reload Now]    25 Total Beds    Occupied: 3

Dirty: 3    (1 in progress)

— 260
— 262
— 266

| | | | | Status | Paged Bed | Now Cleaning | Est. Discharge – Mon 4:00 PM | | | |
|---|---|---|---|---|---|---|---|---|---|---|
| 10 | 3 | 3 | 1005 | stat | in progress | 19 / 10 / 0 min | | | | John Doe |
| 10 | 3 | 3 | 1003 | stat | in progress | 20 / 0 / 0 min | | | | John Doe |
| 10 | 3 | 3 | 1006 | stat | in progress | 19 / 0 / 9 min | | | | stevesf1@hhs1.com.bw2 |
| 10 | 3 | 3 | 1006 | stat | in progress | | | | | |

| Cleaner | Status | | Last Cleaned | Budget | Done | Pager |
|---|---|---|---|---|---|---|
| Mary Doe | free | | 2003 | 0 | 5 | Josh SMS |
| John Doe | statpage | 1005 | 1005 | 0 | 4 | Josh SMS |

| Bed State | Cleaner State | | | | | |
|---|---|---|---|---|---|---|
| | Free | On Break | Paged | In Progress | Paged to Stat | In Progress on Stat |
| Dirty | YES | NO <queued> | NO <queued> | NO <queued> | NO <queued> | NO <queued> |
| Stat | YES | NO <queued> | YES | YES | NO <queued> | NO <queued> |

Transport Request

Acme Hospital | Refresh In: 22 | Refresh Now
602

Transport Type: Patient
604

Patient Name:
Patient ID:
Priority: Normal
Isolation: --None--
Mode of Travel: --None--
(If Other)
Notes:

☐ Oxygen          ☐ IV
☐ Bring Nurse     ☐ Bring Family
☐ Cannot Lie Flat ☐ Cannot Stand
☐ Bedrest         ☐ Up with Assistance
☐ LTAC / Bring Both Charts

600

606

Requester Name:
Requester Extension:

Transport Date/Time Needed:
● Now  ○ Later

608

From Unit: Unit          To Unit: Unit
From Bed: Bed            To Bed: Bed

Submit Request

Transport Assignments

Acme Hospital

| Transporter Name | Pager Name |
|---|---|
| Johnny Black<br>Newt Johnson<br>Speed Wheelington | txDevice SMS Josh<br>txWeb Device |
| 642 | 644 |

[Test Selected Pager] 648

640

| Action | Transporter | Pager | Status | Break Minutes | Transports Completed |
|---|---|---|---|---|---|
| ☐ Unassign | Johnny Black | Test Web Device | free | | 0 |
| ☐ Unassign | Speed Wheelington | | in_progress | | 3 |

[Unassign Selected Assignments] 646

FIG. 19

Acme Hospital | Refresh: 51 | [Reload Now] [Dispatch Request]

Mode: Crowdsource  660                                    [Cancel Request]

662

| Job ID | Time Needed | State | From Unit | From Bed | To Unit | To Bed | Transporter |
|---|---|---|---|---|---|---|---|
| 4681 | 12:06 PM | en route | Unit A | 1005 | radiology | xray1 | Speed Wheelington |
| 4683 | 12:07 PM | requested | Unit A | 1010 | physical therapy | | All Notified |
| 4682 | 12:13 PM | claimed | radiology | xray2 | Unit B | 2006 | Speed Wheelington |
| 4684 | 12/22/2011 | scheduled | Unit A | 1001 | Unit B | 2005 | |

670

| Transporter | Status | Paged To | Now Moving | Last Moved | Done | Pager |
|---|---|---|---|---|---|---|
| Speed Wheelington | in_progress | | 4681 | | 3 | |
| Johnny Black | free | | | | 0 | Test Web Device |

Transport Rescheduler

*Acme Hospital*

700

| | |
|---|---|
| Job Request: | 4684 |
| Requester Name: | joshg    702 |
| Requester Extension: | |
| From: | Unit A - 1001 |
| To: | Unit B - 2005 |

Currently Scheduled for:  12/22/2011 5:30 PM

704

New Date Needed: [ 12/22/2011 ] [ 12/19/2011 ]

New Time Needed: [ 5 ▸ ] [ 30 ▸ ] [ PM ▸ ]

[ Update Request ]

FIG. 22

*Transport Patient Return*

720

Original Transport Request

722

| | |
|---|---|
| Job#: | 4681 |
| Requester Name: | joshg |
| From: | Unit A 1005 |
| To: | radiology xray1 |
| Scheduled: | 12/19/2011 12:06 PM |
| Completed: | 12/19/2011 12:38 PM |

720

New Transport Request

724

| | |
|---|---|
| Scheduled For: | Now |
| From: | radiology xray1 |
| To: | Unit A 1005 |

Enter Patient Id to confirm: _____ 726

[Submit Request]

Transport Type: Patient Return ▼  740

| Action | Request | Requester | Requested | Completed | From Location | To Location |
|---|---|---|---|---|---|---|
| Return Patient | 16893 | april | 06:24 AM | 08:17 AM | 2NE - 205 | Dialysis |
| Return Patient | 16894 | april | 06:27 AM | 07:16 AM | 3NE - 303 | Dialysis |
| Return Patient | 16895 | april | 06:28 AM | 06:50 AM | 4NW | Dialysis |
| Return Patient | 16896 | april | 06:30 AM | 07:04 AM | 3NE - 315 | Dialysis |
| Return Patient | 16906 | julie | 07:15 AM | 07:45 AM | 3NE - 327 | Radiology – X-Ray |
| Return Patient | 16905 | Rayne | 07:35 AM | 08:05 AM | 2NW - 237 | Radiology – Special Procedures |
| Return Patient | 16914 | Denny | 07:53 AM | 08:10 AM | 2NE - 218 | Radiology – Ultra Sound |
| Return Patient | 16915 | mike | 07:53 AM | 08:04 AM | Radiology – X-Ray | 3NE - 327 |
| Return Patient | 16919 | mike | 07:56 AM | 08:23 AM | 2NW - 242 | Radiology – X-Ray |
| Return Patient | 16920 | mike | 07:57 AM | 08:22 AM | 2NW - 245 | Radiology – X-Ray |
| Return Patient | 16923 | russell | 08:20 AM | 08:33 AM | 2NE - 215 | Radiology – MRI |
| Return Patient | 16927 | Denny | 08:26 AM | 08:32 AM | Radiology – Ultra Sound | 2NE - 218 |
| Return Patient | 16928 | mike | 08:29 AM | 08:41 AM | Radiology – X-Ray | 2NW - 245 |
| Return Patient | 16929 | joel mire | 08:34 AM | 08:38 AM | Radiology – X-Ray | 2NW - 242 |
| Return Patient | 16930 | Rayne | 08:47 AM | 09:04 AM | Radiology | 2NW - 237 |
| Return Patient | 16908 | peter | 08:50 AM | 08:54 AM | 5NE - 515 | Radiology – Oncology |
| Return Patient | 16931 | russell | 08:51 AM | 09:06 AM | Radiology – MRI | 2NE - 215 |
| Return Patient | 16934 | GEORGE | 09:05 AM | 09:16 AM | SDS | Radiology – Nuclear Med |
| Return Patient | 16935 | peter | 09:16 AM | 09:38 AM | Radiology – Oncology | 5NE - 515 |
| Return Patient | 16937 | GEORGE | 09:30 AM | 09:36 AM | Radiology – Nuclear Med | SDS |
| Return Patient | 16940 | julie | 09:47 AM | 10:11 AM | 2NE - 232 | Radiology – X-Ray |
| Return Patient | 17001 | amanda | 10:19 AM | 10:29 AM | Radiology – X-Ray | 2NE - 232 |
| Return Patient | 17004 | manda | 10:39 AM | 11:03 AM | ER - 9 | Cat Scan |
| Return Patient | 17007 | april | 11:02 AM | 11:25 AM | 2NW - 237 | Dialysis |
| Return Patient | 17008 | april | 11:03 AM | 11:40 AM | Dialysis | 4NW - 441 |
| Return Patient | 17009 | april | 11:04 AM | 11:54 AM | Dialysis | 3NE - 315 |
| Return Patient | 17012 | manda | 11:10 AM | 11:18 AM | Cat Scan | ER - 9 |

Acme Hospital
Performance — 3rd Shift Transporter
November 3

| Transporter | Calls completed | Average Response Time (minutes) | Total Distance Traveled (km) | Average Job Difficulty | Time on break (minutes) | Current Score |
|---|---|---|---|---|---|---|
| Speed Wheelington | 6 | 13 | 1.6 | 3.5 | 20 | 6.8 |
| Cass Stevenson | 4 | 14 | 1.3 | 4.8 | 16 | 6.4 |
| Johny Black | 5 | 16 | 1 | 3 | 20 | 6.1 |
| Tara Smith | 4 | 18 | 0.9 | 2 | 28 | 5.7 |
| Sam Slower | 1 | 24 | 0.2 | 2 | 65 | 4.2 |

FIG. 34

SYSTEM AND METHODS FOR PROVIDING TRANSPORTATION SERVICES IN HEALTH CARE FACILITIES

PRIORITY CLAIM

This application claims priority to U.S. Provisional Application Ser. No. 61/587,502 entitled "SYSTEM AND METHODS FOR PROVIDING TRANSPORTATION SERVICES IN HEALTH CARE FACILITIES" filed Jan. 17, 2012, which is incorporated herein by reference in its entirety.

BACKGROUND

Field

The present disclosure relates generally to the managing and providing services in health care facilities. More particularly, aspects of the present disclosure relate to systems and methods for assigning and directing personnel and managing workflow in health care facilities.

Description of the Related Art

Caring for patients in health care facilities requires a substantial amount of medical and non-medical services. In addition to medical staff, many other members of a health care facility's staff provide services to attend to the needs of patients in the facility and to maintain the facility in continuous operation. Such services include transportation, housekeeping, environmental services ("EVS"), bed management, facilities management, admission/discharge/transfer administration, security, and human resources.

In a health care facility setting, some services will be designated as "stat", or urgent. Typically, a stat designation is made for an action that must be taken promptly in order to meet the urgent needs of a patient or to keep the facility operating at full capacity. From the standpoint of an employee, responding to stat requests may be more stressful than ordinary requests because the employee is under more pressure to complete the task quickly. In many cases, a stat request may be associated with an urgent medical situation, such as cardiac arrest or another emergency situation.

In many health care facilities, computer systems are used to help manage services provided to patients. In some health care facilities, requests for some services, such as bed cleaning or patient transport, are triggered by messages from an Admission Discharge Transfer ("ADT") system. For example, a message from an ADT system that a patient has just been discharged from the room may trigger a bed cleaning request.

Some existing computer systems for managing services in health care facilities, such as services for transport of patients or equipment, may not assign tasks or use the resources available in the facility an efficient or timely manner. For example, some computer systems may make assignments and communicate information in a manner that results in too many or too few resources being placed on given task, or in a disproportionate burden being borne by some staff members of the facility.

SUMMARY

Systems and methods for managing and providing services in health care facilities are described. In an embodiment, a system for providing transportation services in a health care facility includes a communication network, a transportation services management system, one or more dispatcher devices, and one or more transport responder mobile devices. The transportation services management system stores and retrieves information relating to dispatches of transportation services jobs at one or more health care facilities. The dispatch devices exchange, with the transportation services management system, information relating to the transportation services jobs and display information to a transportation dispatch manager. The transport responder mobile devices exchange, with the transportation services management system, information relating to the transportation services jobs and display information to transport responders.

In an embodiment, a method for providing transportation services in a health care facility includes sending to mobile devices a notification about a transportation services job and the notification on the mobile devices. A response relating to the transportation services job is received by way of the mobile devices. A responder is assigned to the transportation services job by way of one of the mobile devices.

In one embodiment, a tangible, computer readable medium includes program instructions are computer-executable to implement a method for providing transportation services in a health care facility includes sending to mobile devices a notification about a transportation services job and the notification on the mobile devices. A response relating to the transportation services job is received by way of the mobile devices. A responder is assigned to the transportation services job by way of one of the mobile devices.

In an embodiment, a method for method for providing transportation services in a health care facility includes sending, to two or more candidate responders, a notification of a transportation services job and displaying information about the transportation services job to the candidate responders. A response is received from the candidate responders relating to the transportation services job. A responder is assigned to the transportation services job based on the responses to the job notification. The number of responders assigned to the transportation services job is based on pre-determined criteria (such as a maximum cut-off number of responders). In certain embodiments, the job notification is crowd sourced to the candidate responders by way mobile devices on a communication network.

In one embodiment, a system includes a processor and a memory coupled to the processor, wherein the memory stores program instructions executable by the processor to implement a method for method for providing transportation services in a health care facility includes sending, to two or more candidate responders, a notification of a transportation services job and displaying information about the transportation services job to the candidate responders. A response is received from the candidate responders relating to the transportation services job. A responder is assigned to the transportation services job based on the responses to the job notification. The number of responders assigned to the transportation services job is based on pre-determined criteria (such as a maximum cut-off number of responders). In certain embodiments, the job notification is crowd sourced to the candidate responders by way mobile devices on a communication network.

In one embodiment, a tangible, computer readable medium includes program instructions are computer-executable to implement a method for method for providing transportation services in a health care facility includes sending, to two or more candidate responders, a notification of a transportation services job and displaying information about the transportation services job to the candidate responders. A response is received from the candidate responders relating to the transportation services job. A responder is assigned to the transportation services job based on the responses to the job notification. The number of responders assigned to the transportation services job is based on pre-determined criteria (such as a maximum cut-off number of responders). In certain embodiments, the job notification is crowd sourced to the candidate responders by way mobile devices on a communication network.

In an embodiment, a method for managing the provision of services in a health care facility includes sending notifications about tasks to two or more staff members. Information about the tasks is displayed to the staff members. A response relating to the task is received over the network from at least one of the staff members. A staff member is assigned to the tasks based on the responses to the task notifications. Performance or responsiveness information of the staff members is displayed to staff members over the network. In certain embodiments, the staff members participate in a game based on performance or responsiveness of the staff members.

In one embodiment, a system includes a processor and a memory coupled to the processor, wherein the memory stores program instructions executable by the processor to implement a method for managing the provision of services in a health care facility includes sending notifications about tasks to two or more staff members. Information about the tasks is displayed to the staff members. A response relating to the task is received over the network from at least one of the staff members. A staff member is assigned to the tasks based on the responses to the task notifications. Performance or responsiveness information of the staff members is displayed to staff members over the network. In certain embodiments, the staff members participate in a game based on performance or responsiveness of the staff members.

In one embodiment, a tangible, computer readable medium includes program instructions are computer-executable to implement a method for managing the provision of services in a health care facility includes sending notifications about tasks to two or more staff members. Information about the tasks is displayed to the staff members. A response relating to the task is received over the network from at least one of the staff members. A staff member is assigned to the tasks based on the responses to the task notifications. Performance or responsiveness information of the staff members is displayed to staff members over the network. In certain embodiments, the staff members participate in a game based on performance or responsiveness of the staff members.

BRIEF DESCRIPTION OF THE DRAWINGS

FIG. 3 illustrates one embodiment of a system of health care facilities connected over a network to a cloud computing system.

FIG. 4 illustrates one embodiment of an electronic bed board.

FIG. 5 illustrates one embodiment of a user interface for managing environmental services.

FIG. 6 illustrates one embodiment of a user interface for an EVS manager dispatch.

FIG. 8 illustrates one embodiment of a truth table for making bed cleaning assignments.

FIG. 17 illustrates one embodiment of an input screen for receiving patient transportation requests.

FIG. 18 illustrates one embodiment of an input screen for equipment transportation requests.

FIG. 19 illustrates one embodiment of transportation assignments board display.

FIG. 20 illustrates one embodiment of a dispatch board for transport jobs.

FIG. 22 illustrates one embodiment of a rescheduler screen for transport requests.

FIG. 23 illustrates one embodiment of a patient return screen for transport requests.

FIG. 24 illustrates one embodiment of a status reporting screen for transportation services.

FIG. 30 illustrates a user menu for a making a selection on a job.

FIG. 31 illustrates a user menu for a screen for managing a transport delay over a mobile device.

FIG. 34 illustrates one a display board showing statistics and scores for a group of transporters according to one embodiment.

Figure 1:
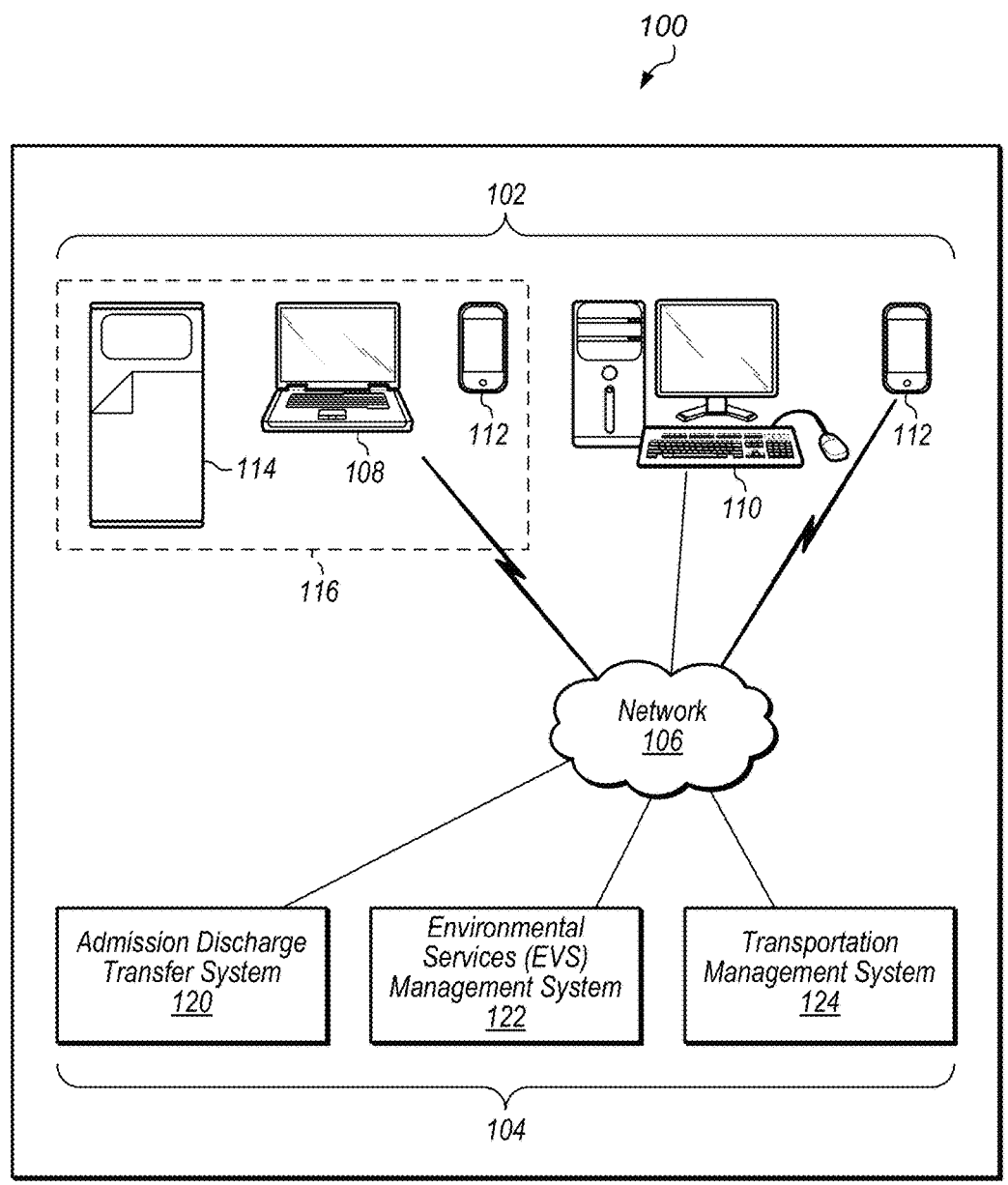
FIG. 1 illustrates one embodiment of a health care services system including management systems connected to user devices over a network.

While the invention is described herein by way of example for several embodiments and illustrative drawings, those skilled in the art will recognize that the invention is not limited to the embodiments or drawings described. It should be understood, that the drawings and detailed description thereto are not intended to limit the invention to the particular form disclosed, but on the contrary, the intention is to cover all modifications, equivalents and alternatives falling within the spirit and scope of the present invention as defined by the appended claims. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including, but not limited to.

DETAILED DESCRIPTION OF EMBODIMENTS

As used herein, an "action" means an act, task, milestone, operation, step, process, or communication that can be performed, completed, or achieved by one or more persons.

As used herein, "call message" means a message that requests, directs, or commands an action to be carried out by one or more persons, or indicates a need for an action by one or more persons.

As used herein, "candidate" means a person who may be considered for a task.

A "communications network" refers to a system including one or more communication channels (i.e., lines, satellite frequency, radio waves, etc.) interconnecting one or more nodes (i.e., servers, routers, computers, communication devices, etc.). Examples of a "communications network" include a cellular telephone network, the internet, a local area network (LAN), or a wide area network (WAN).

As used herein, "fictional" message means a message that is initiated or entered into a system by user even though the message is known to not reflect actual conditions or needed actions. A fictional message may be entered for administrative purposes, such as for billing, operations, or logistics.

As used herein, "health care facility", includes any facility in which medical health care services are provided. Examples of a health care facility includes a hospital, a Federally qualified health center, a rural health clinic, a nursing home, personal care home, a home health agency, a hospice program, a public health clinic, a State or local department of public health, a skilled nursing facility, an ambulatory surgical center.

As used herein, an "HL7" message means a message based on an HL7 standard, such as the HL7 version 2.x or HL7 version 3 standard developed by the Health Level Seven community.

As used herein, a "misleading message" is a message that is false, fictional, or otherwise misleading. A misleading message may indicate or suggest that a condition exists (such as a discharge of a patient from a hospital room) when the condition does not in fact exist, or is intended or likely to be reversed or cancelled. A misleading message may also indicate or suggest that an action (such as a bed cleaning) should be undertaken when no such action is or will be required. In some embodiments, a misleading message may indicate that a bed is occupied when it is in fact not occupied, or, conversely, that a bed is not occupied when it is in fact occupied. In certain embodiments, a misleading message is the result of bed hiding. A misleading message may include an ephemeral or fleeting message that is temporarily true, but with the intention, expectation, or likelihood of being reversed, cancelled, or superseded.

As used herein, "misleading message pattern" means a pattern in a set or group of two or more messages that indicates or suggests that at least one message in the set or group of messages is a misleading message.

As used herein, "occupant" means a person who is occupying a room or area. An occupant may be a patient in a hospital room.

As used herein, to "page" means to send a message to one or more persons to notify the person of one or more actions.

As used herein, "request" means a request to do a task, or an indication that a task should be performed. For example, a cleaning request may be a message indicating that one or more beds are dirty and need to be cleaned.

As used herein, "task" includes a specific task, set of tasks, a shift, or duties.

As used herein, "stat" means urgent or rush.

As used herein, "suspect" message means a message that has at least one characteristic making it appear suspicious, or indicating or suggesting that it could be misleading.

As used herein, "unhold" means to release a message from a hold condition.

In various embodiments, a system for managing services in a health care facility includes user devices connected to management systems over a network. FIG. 1 illustrates one embodiment of a health care services system including management systems connected to user devices over a network.

System 100 includes user devices 102, management systems 104, and network 106. User devices 102 may be connected with one another and with management systems 104 over network 106. Management systems 104 may be connected with one another by way of network 106. In various embodiments, system 100 may be used to manage and provide services in a health care facility, such as a hospital.

User devices 102 include notebook computer 108, desktop computer 110, and portable electronic devices 112. Examples of portable electronic devices include a smart phone, a tablet computer, or a pager. User devices 102 may enable communication, task management, and reporting between one another and between other systems on network 106.

User devices 102 may be connected to the network over any suitable medium, such as electrical or optical cable, or via any suitable wireless standard such as IEEE 802.11 ("Wi-Fi"), IEEE 802.16 ("WiMax"), or cellular network.

In some embodiments, user devices connected via a network are operated from patient rooms in a health care facility. For example, as illustrated in FIG. 1, notebook computer 108 may be located in room 116. Notebook computer 108 may be operated in connection with management of bed 114.

Management systems 104 include admission/discharge/transfer ("ADT") system 120, environmental services ("EVS") management system 122, and transportation management system 124. ADT system 120 may be used to manage patient admissions, discharges, and transfers in a health care facility, such as admission, discharge, and transfer of a patient in room 116.

EVS management system 122 may be operated to manage environmental services in a facility. Examples of environmental services may include bed cleaning, room cleaning, housekeeping, disinfection, decontamination, room supplies, or laundry. In some embodiments, EVS management system 122 receives and responds to messages sent from ADT system 120. For example, EVS management system 122 may generate cleaning request for a room in response to receiving a patient discharge notice from ADT system 120. The discharge message may be sent over network 106.

In FIG. 1, ADT system 120, EVS management system 122, and transportation management system 124 are depicted as a separate systems. Any or all of these systems may, however, be combined in some embodiments into one computer system, such as a management server. In one embodiment, ADT system 120 is provided on one computer system and EVS management system 122 and transportation management system 124 are provided on a second computer system. In some embodiments, EVS management system 122 and transportation management system 124 receive HL7 messages issued from ADT system 120.

Transportation system 124 may be operated to manage transportation services at a facility. Examples of transportation services may include transporting a patient from one location to another, transporting equipment from one location to another, or transporting items for medical procedures or testing. A patient or resident of a facility may be transported into a facility to another location, from another location to the facility, or from one location to another within a facility, such as from one room to another room in a hospital. Equipment may include systems for providing medical treatment or diagnosis, such as an x-ray machine, ultrasound machine, surgical table, or treadmill. Medical items may include medicine, plasma, blood samples, or transplant organs.

Although for illustrative purposes only a single notebook computer and a single desktop computer are shown in FIG. 1, a system may in various embodiments have any number, and any of various types, of portable or fixed electronic devices.

For illustrative purposes, FIG. 1 shows user devices including a notebook, smart phone, and desktop workstation. Nevertheless, in various embodiments, other types of user devices may be used by cleaners and other personnel. For example, each cleaner on the staff of a hospital may carry a pager. As another example, a cleaner may access information relating to the cleaner's assignments from a fixed workstation, such as a personal computer workstation in an occupant's room. In certain embodiments, the portable electronic devices connected to a system include tablet computers or smart phones.

In some embodiments, a bed management system is integrated with an ADT system, an EVS management system 122, or both. For example, a bed management system may be integrated with ADT system 120.

Figure 2:
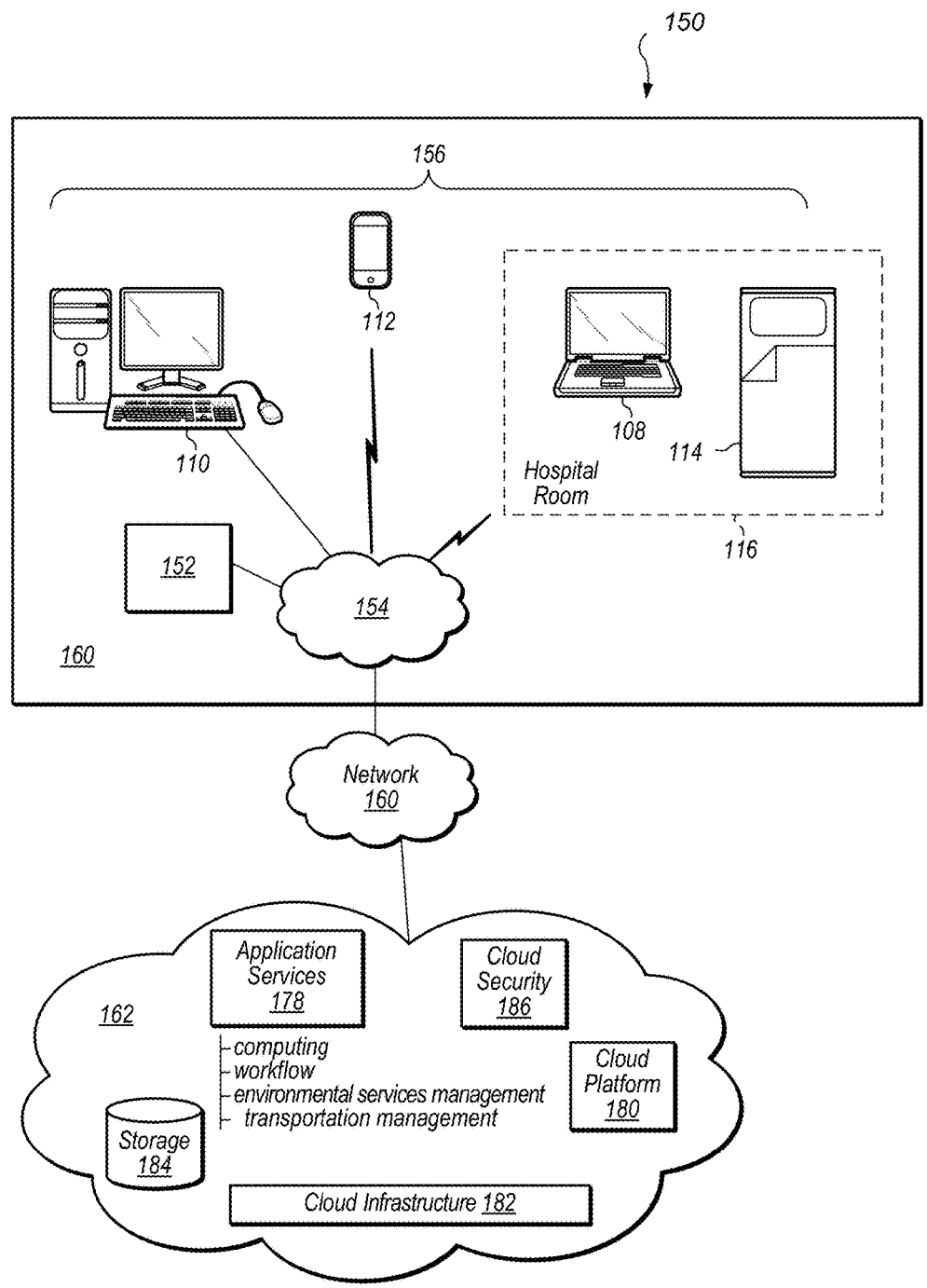
FIG. 2 illustrates one embodiment of a system including a hospital with a network connection to a cloud computing system.

In some embodiments, management of a health care facility includes accessing a cloud computing system over a communications network. FIG. 2 illustrates one embodiment of a system including a hospital with a network connection to a cloud computing system. System 150 includes hospital computing system 152, network 154, and user devices 156. Hospital computing system 152 and user devices 156 may be connected by way of network 154. Hospital computing system 152, network 154, and user devices 156 may be located at site 160. Hospital computing system 152 and user devices 156 may be connected to cloud computing system 162 by way of network 160. Hospital personnel may operate user devices 156 to access hospital computing system 152 and cloud computing system 162.

Networks 154 and 160 may include any suitable data network or combination of networks that enable the exchange of information between electronic systems. For example, networks 160 may include one or more Local Area Networks (LANs) such as Ethernet networks, as well as Wide Area Networks (WANs), Metropolitan Area Networks (MANs), or other data or telecommunication networks implemented over any suitable medium, such as electrical or optical cable, or via any suitable wireless standard such as IEEE 802.11 ("Wi-Fi"), IEEE 802.16 ("WiMax"), etc. In various embodiments, all or a portion of networks 160 may include the network infrastructure commonly referred to as the Internet. In other embodiments, networks 154 and 160 may be entirely contained within an enterprise and not directly accessible from the Internet. In certain embodiments, information may be exchanged over a virtual private network. In one embodiment, information is exchanged over the internet, but encrypted in such a way to make a private network not accessible from the rest of the internet.

Cloud computing system 162 may provide remote computing resources, remote storage resources, or both, for systems connected to cloud computing systems 162. For example, cloud computing system 162 may provide cloud computing services to personnel at site 160.

Various system architectures may be employed in cloud computing system 162. Systems and components of cloud computing system 162 may be at a single physical location, such as a data center, or distributed among any number of locations. Cloud computing system 162 includes cloud application services 178, cloud platform 180, cloud infrastructure 182, cloud data storage 184, and cloud security 186. Examples of application services 178 include computing services, remote data storage services, workflow management, production control, content management, accounting, administration, human resources, and enterprise resource planning. Cloud application services 178 may access cloud data storage 184.

In some embodiments, some of health facilities services are managed using application services in a computing cloud. In one embodiment, environmental services, transportation services, or both, are performed as one of application services 178. In certain embodiments, environmental services or transportation services in a cloud receive a message feed from a local computing system, such as one or more of systems 204 at sites 202. In one embodiment, system 204 includes an ADT system that transmits HL7 messages to application services in cloud computing system 162.

Cloud infrastructure 182 may encompass a variety of physical resources, such as computing devices, servers, block storage, mass storage devices, file servers, software, and network systems. In some embodiments, a cloud computing system encompasses virtualized resources, such as virtualized data storage or virtualized hardware.

In some embodiments, a service provider provides resources to customers by way of cloud computing resources. In some embodiments, computation resources are rented or leased to customers of the service provider. In certain embodiments, services are provided to users at sites as software as a service ("SaaS") or platform as a service ("Paas"). Services may be provided to each customer on an on-demand basis.

FIG. 3 illustrates one embodiment of a system of health care facilities connected over a network to a cloud computing system. System 200 includes health care sites 202 includes site 1 through site n. Each of sites 202 may include a site computing system 204. Site computing systems 204 may include, for example, a network of computing devices distributed at the site and connected to one another by way of network 206. Each of site computing systems 204 may be connected to cloud computing system 162 by way of network 210. Cloud computing system 162 may be similar to the cloud computing system described above relative to FIG. 2. In certain embodiments, site computing systems 204 may be connected to one another by way of network 210.

In various embodiments, some of sites may be connected over a different network than other sites. For example, as shown in FIG. 3, Site n may be connected to cloud computing system 162 over network 212. In some embodiments, one or more sites are connected over a private network. For example, in the embodiment shown in FIG. 3, network 210 may be a public network and network 212 may be a private network.

In various embodiments, a user may communicate over systems in system 200 from locations external to sites 202 and cloud computing system 176. For example, users not located at one of sites 202 may communicate with users at sites 202 by way of portable electronic devices 220. Portable electronic devices 220 may be located anywhere, including a manager's, administrator's, or physician's home, a health clinic, or any other location.

Although for illustrative purposes only three sites are shown in FIG. 3, a system may include any number of sites and any number of site computer systems. In some embodiments, one site has two or more site computer systems.

In some embodiments, a system for managing services in a health care facility includes one or more electronic bed boards. Electronic bed boards may be accessed and displayed on one more computer systems in a health care facility. In some embodiments, each user is authenticated (such as by login or access card) before access is to the system is provided.

In some embodiments, a bed board is accessible to a user on a portable electronic device. In certain embodiments, a bed board is accessible to a user by way of a smart phone. Users may review bed board information, make or accept assignments, or enter information relating to specific personnel, cleaning services, rooms or assignments.

In some embodiments, a Summary Bed Board view provides information relating to the status of beds/rooms and their availability. A view may include a combination of two or more of: (1) Number of Clean Beds; (2) Number of Needed Beds; (3) The Sex of Patients Waiting for Beds; (4) Listing of Beds Currently Available; (5) Listing of Beds Available Soon; and (6) Sex Corresponding to the Beds Available and Available Soon.

FIG. 4 illustrates one embodiment of an electronic bed board. Electronic bed board 240 includes summary box 242 and unit panels 244. A separate unit panel 244 may be provided for each unit in a facility (for example, a hospital unit). Each of unit panels 244 may include room listing 246 and unit summary 248. Each row of the listing may include information on a bed in the identified room. The following notes reflect examples of information that may be included in a room listing in various embodiments.

Bed 1002. "Cont" may indicate one of 3 generic isolation conditions (contact, droplet, airborne). Isolation condition information may be important to cleaners because they must protect themselves differently for different isolation condition types. An indication that a room is ISO may also appear in a cleaner's pager message Bed 1005. 15/6/0 may indicate that the room has been dirty for 15 minutes, and was marked as stat 6 minutes ago Bed 1006. 15/0/6 may indicate that the room has been dirty for 15 minutes, 0—never marked as stat, cleaning started 6 minutes ago.

Bed 1007. A grey color may indicate that the room is not available for use. Comments may indicate nature of the problem ("Ants in room").

Bed 1008. Hospital staff has noted the likely discharge time at 4 pm Monday.

Summary box 242 includes facility drop down menu 249. Facility drop down menu 249 may allow a user to change between bed boards of different health care facilities.

In some embodiments, a computer system includes a user interface for managing environmental services. In one embodiment, an environmental services bed board includes of a view of one or more of following information: (1) Number of Beds; (2) Number of Clean Beds; (3) Number of Occupied Beds; (4) Number of Dirty Beds; (5) Time Beds Have Been Dirty; (6) Cleaner(s) Assigned; (7) Cleaners Available; (8) Duration of Pending Cleaning Request; (9) Duration of STAT Cleaning. (10) Last Time Bed/Room Cleaned; and (11) Last Cleaner to Clean Bed/Room.

FIG. 5 illustrates one embodiment of a user interface for managing environmental services. EVS Manager 260 includes EVS management panel 262. EVS management panel 262 includes room summary 264, room listing 266, and cleaner listing 268.

In room listing 266, the second, third, fourth columns indicate how many beds, occupied beds, and clean beds are in the same unit as the bed shown on that row. If a bed is in a unit that contains many other clean beds, service for that bed is not likely to be a stat job. On the other hand, if there are no other clean beds in the unit, then service for that bed may be a stat job.

In some embodiments, some or all of the cleaners on a list of cleaners may include a visual indication that shows how busy the cleaner is. For example, a color may be shown on each cleaner's name column to indicate how busy the cleaner is. Each color in a set of colors may indicate a different level of business for a cleaner.

Figure 6:
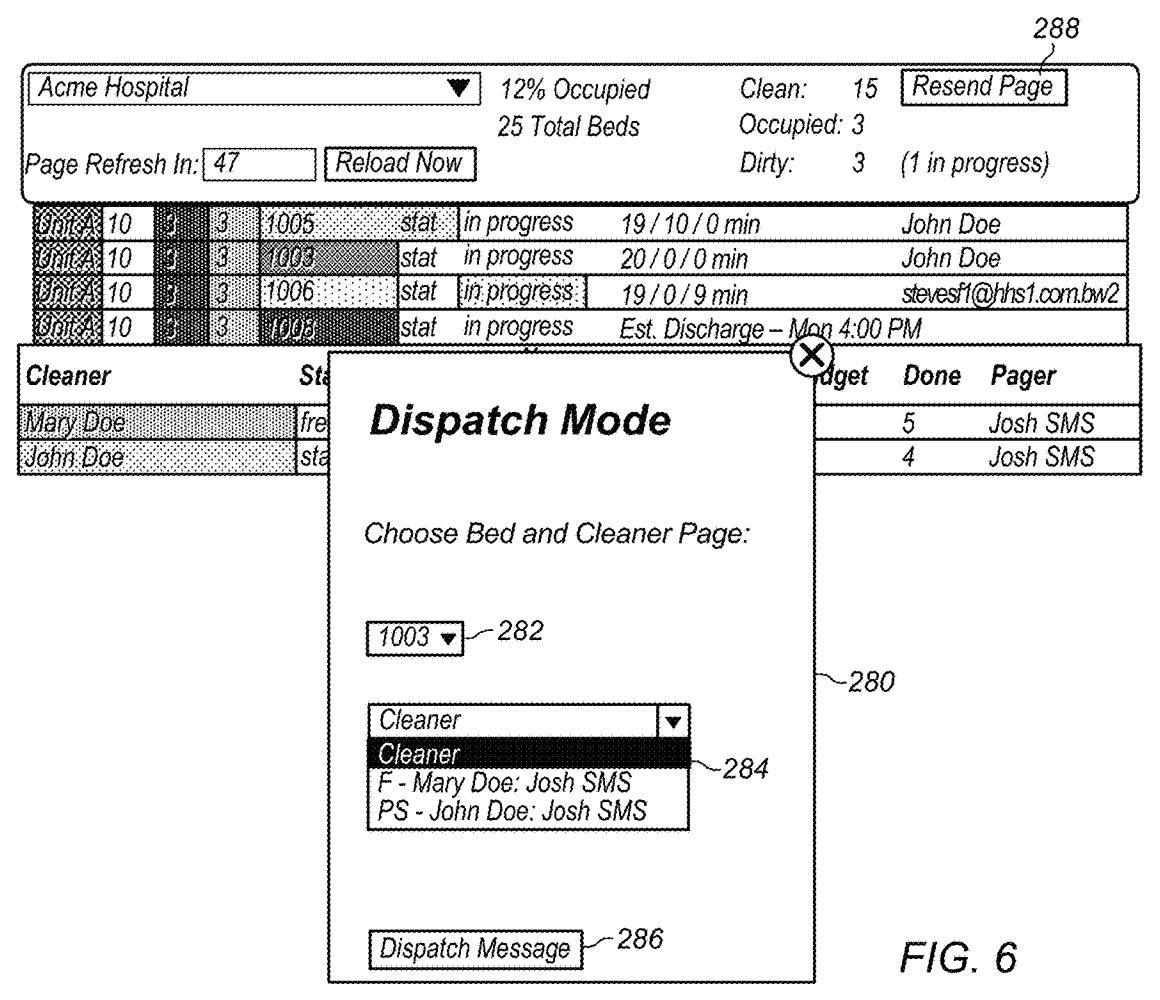

In some embodiments, a manager activates a dispatch window from a dual-pane management window for managing EVS services. FIG. 6 illustrates one embodiment of a user interface for an EVS manager dispatch. Dispatch mode window 280 may be overlaid on an EVS management panel, such as EVS management panel 262 shown in FIG. 5. Dispatch mode window 280 includes bed drop down menu 282, cleaner drop down menu 284, and dispatch button 286.

If a manager clicks resend page 288, the manager can do a manual dispatch. A manual dispatch may include:
selecting a room
selecting a cleaner for the room
dispatching a dispatch message In some embodiments, an indicator, such as a code, is displayed in association with each cleaner's name that indicates how busy the cleaner is. The listing of cleaners may be sorted based on how busy the cleaners are. In some embodiments, the listing is sorted from least busy to most busy. The manager picks from someone from the top of the list because they are sorted as less busy. An example set of codes is listed below.
F—free
P—paged
I—in progress
PS—paged to a stat room
IS—in progress on a stat room In progress on a stat may be sorted to the bottom of the listing. In certain embodiments, cleaner status may be indicated using different colors (for example, green for free, red for unavailable).

After selecting a room and a cleaner, the manager may click on dispatch button 286 to automatically generate a dispatch message.

In some embodiments, a user manages services in a health care facility using a portable electronic device. In one embodiment, a portable electronic device includes a portable housing, a processor, and input device (such as a touch screen), and a display. The display may simultaneously display to a user a request panel that includes one or more cleaning requests and a cleaner panel that includes a list of one or more cleaners. The display may be, for example, a two panel display as described above relative to FIG. 5.

In various embodiments, services in a health care facility are managed using one or more computer systems. Examples of services that may be managed using a computer system include environmental services, cleaning, admission/ discharge/transfer, bed management, or transportation. In some embodiments, services are managed over a user devices connected to a network, such as a portable electronic device.

In some embodiments, a limit is placed on the number of a stat requests assigned to a staff member of a medical or personal care facility. In one embodiment, stat cleaning requests are distributed in a limited manner to reduce the stress level for environmental services (EVS) staff.

Figure 7:
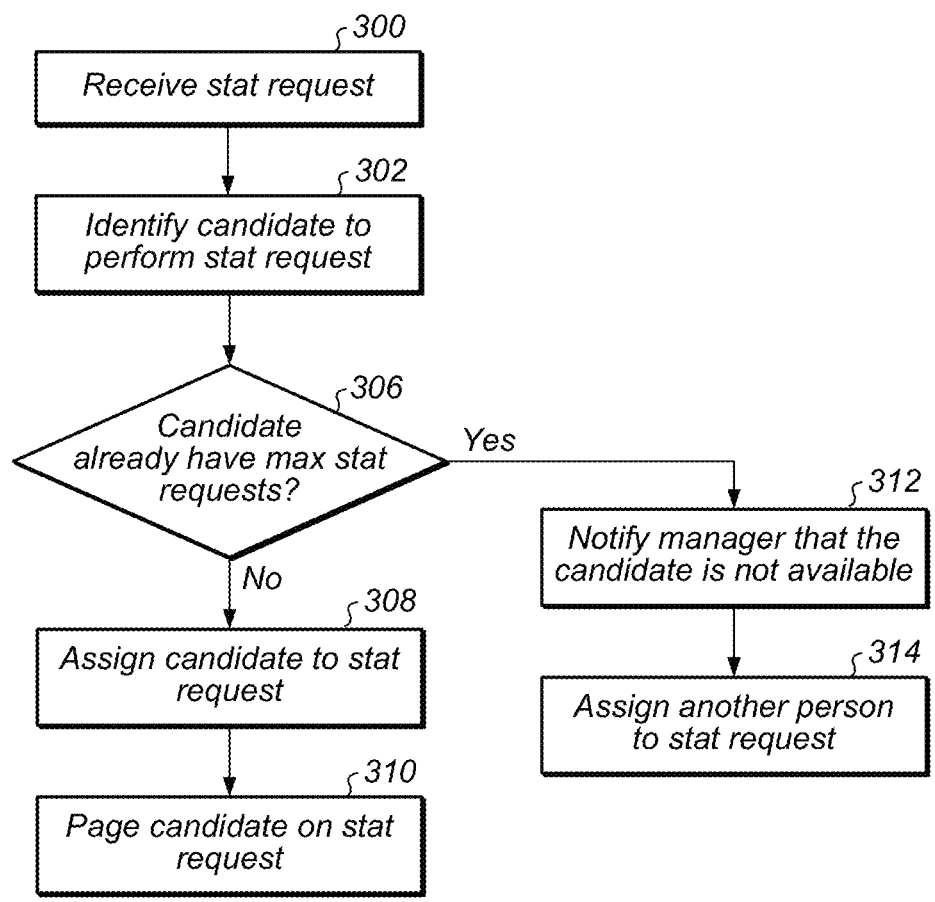
FIG. 7 illustrates one embodiment of managing services that includes a limit on stat requests.

FIG. 7 illustrates one embodiment of managing services that includes a limit on stat requests. At 300, one or more stat requests are received. Stat requests may be, for example, an urgent request to clean a bed or a room. In some embodiments, stat requests are received into a computer system from a dispatch manager.

At 302, one or more candidates are identified to perform a stat request. The candidates may be, for example, cleaners on a hospital staff.

At 304, for at least one of the candidates, a determination is made whether the candidate has a maximum number of stat requests. In some embodiments, the maximum number is a setting that can be set by a manager or administrator for all stat requests that come in. In one embodiment, the maximum number of stat requests is one stat request. In some embodiments, all of the candidate assignments are maintained a computer system. The determination of whether the candidate already has the maximum number of candidates may be made automatically by the computer system.

If the candidate does not have the maximum number of stat requests, the candidate is assigned to the stat request at 308. At 310, the candidate is paged with the assignment.

If the candidate already has the maximum number of stat requests, the stat request is not assigned to the designated cleaner, and a manager is notified that the candidate is not available to respond to the stat request at 312. At 314, a person other than the candidate is assigned to the stat request. Assignments may be made either by a manager or automatically by a computer system.

In some embodiments, candidates and alternate candidates are automatically identified and/or assigned by an automated management system. In certain embodiments, some or all of the candidate cleaners are identified and/or assigned manually (for example, a manager making a selection on an electronic board).

In some embodiments, an escalation process is based on tasks not being initiated within a threshold amount of time. In one embodiment, upon receiving an indication of a dirty room/bed, a designated cleaner is assigned the task of cleaning the dirty room/bed (e.g., via a page to the designated cleaner). The system may monitor whether or not the task has been initiated within a threshold period of time (e.g., whether or not the designated cleaner has indicated starting cleaning of the room/bed within 30 min of the request). If it is determined that the task has been initiated within the threshold period of time, the usual workflow may continue (e.g., the system may wait for an indication of cleaning complete from the designated cleaner). If it is determined that the task has been not been initiated within the threshold period of time, the task may be escalated. For example, a manager may be notified of that the task has not been initiated within the threshold period of time. The task may be reassigned to another cleaner manually (e.g., by the manager) or automatically (e.g., by the system).

In some embodiments, cleaning requests are assigned based on a combination of a bed state and cleaner state. Assignments may be made by rules that implement values in a truth table. FIG. 8 illustrates one embodiment of a truth table for making bed cleaning assignments.

Cleaner truth table 316 includes values for combination of bed state 317 and cleaner state 318. In this example, bed states 317 include dirty or stat. Cleaner states 318 include Free, On Break, Paged, In Progress, Paged to Stat, and In Progress on Stat. In some embodiments, each page message may be sent to the truth table. The value for the combination of bed state 317 and cleaner state 318 may be used to determine how to manage a particular cleaning request. In some embodiments, the value for the combination of bed state 317 and cleaner state 318 determines whether a particular candidate cleaner is assigned a request. For example, if a cleaner has already been paged to a non-stat request, the truth table may be applied based on Paged column 320. If the bed state for the incoming request is stat, the candidate may be assigned the task and paged accordingly. If the bed state for the incoming request is stat, the candidate may be not be assigned the task and the request queued for further processing.

Figure 9:
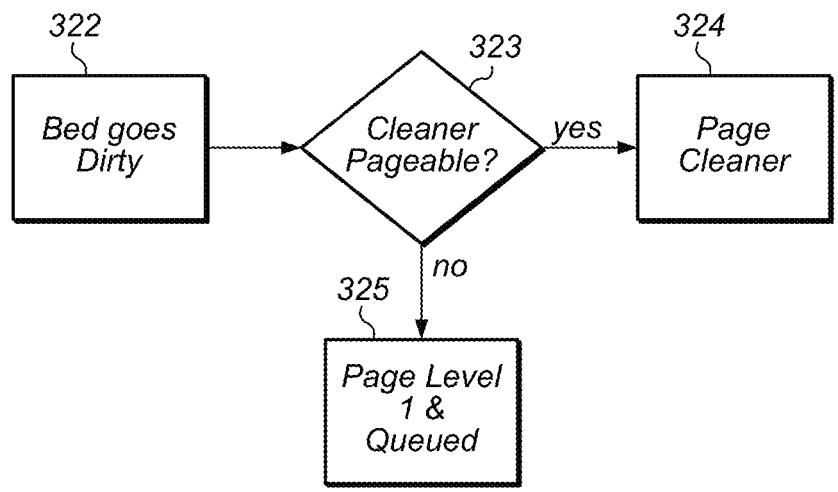
FIG. 9 is a flow diagram illustrating a cleaner page initiated based on a message that a bed has gone dirty.

FIG. 9 is a flow diagram illustrating a cleaner page initiated based on a message that a bed has gone dirty. At 322, an indication is provided that a bed has gone dirty. A bed may go dirty, for example, at the time a patient is discharged from a room in a hospital. At 323, a determination is made whether a cleaner is pageable. In some embodiments, a determination of whether a cleaner is pageable for a particular assignment is based on a combination of a bed state and a cleaner state. For example, a cleaner state of Free may indicate that the cleaner is pageable. As another example, a cleaner state that the cleaner is In Progress on Stat may indicate that the cleaner is not available for any new cleaning assignments. As still another example, a cleaner state of In Progress on a non-stat cleaning request may indicate that the cleaner is pageable for new stat requests, but would not be pageable for non-stat requests.

If a determination made is that the cleaner is pageable, a page is sent to the cleaner at 324. The page may be sent automatically. In cases where the cleaner is indicated as not pageable (for example, due to the pager being In Progress cleaning another room), a cleaning request may be placed in a queue at 325. A Level 1 page may be issued. In some embodiments, a Level 1 page includes a notice to the cleaner or other cleaners that a room is dirty. The queued request may be sent to the cleaner upon completion of the non-stat request, or sent to another cleaner. In various embodiments, the determination of whether the cleaner is pageable, the page, and the queuing of the request are performed automatically by a computer system, such as an EVS management system.

Figure 10:
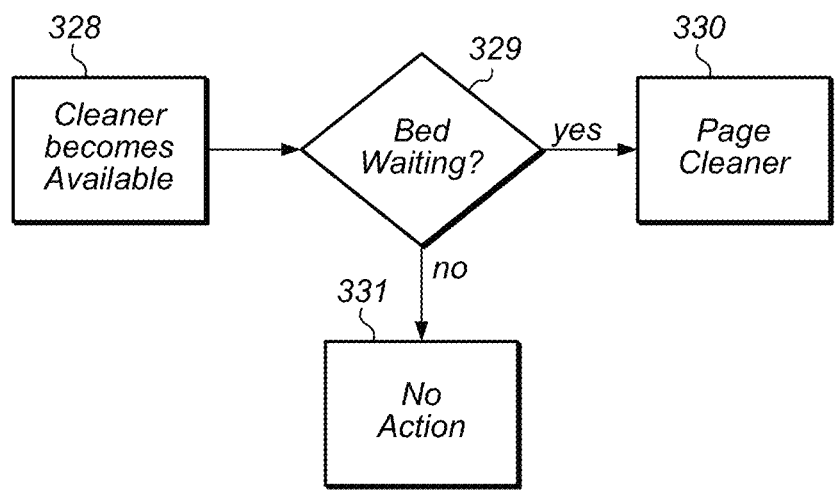
FIG. 10 is a flow diagram illustrating paging based on a message that a cleaner has become available.

In some embodiments, a page of a cleaner is triggered by a message that a cleaner has become available. FIG. 10 is a flow diagram illustrating paging based on a message that a cleaner has become available. At 328, an indication is provided that a cleaner has become available. A cleaner may become available, for example, when the cleaner starts the cleaner's shift, when the cleaner comes off break, or when the cleaner finished a previously assigned task. At 329, a determination is made whether a bed is waiting. A bed waiting may include either a standard bed dirty condition or a stat bed cleaning condition. If a bed is waiting, the available cleaner is paged at 330. If a bed is not waiting, no action is taken at 331.

Figure 11:
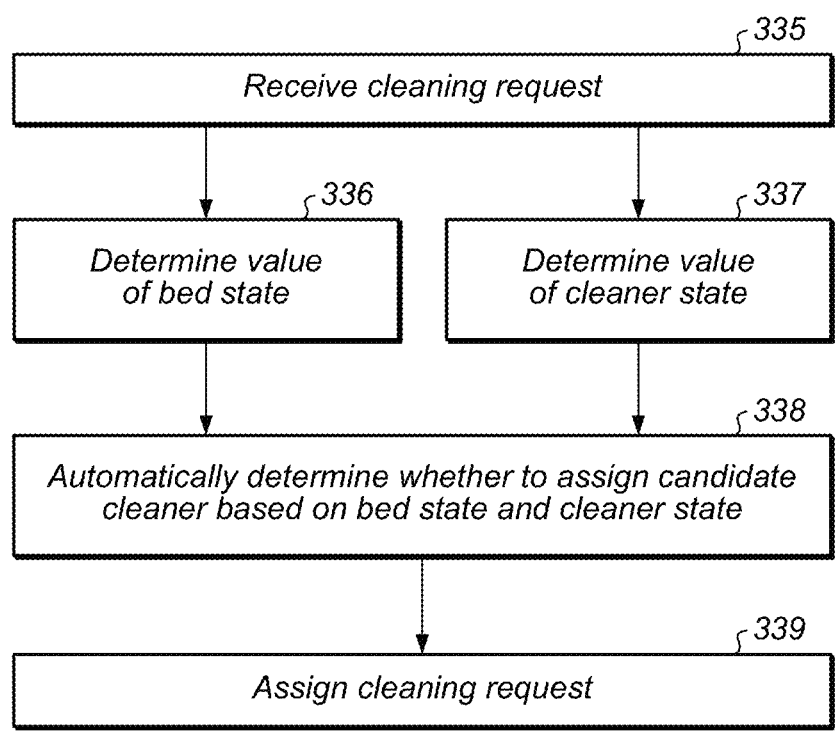
FIG. 11 illustrates one embodiment of making assignments based on a combination of values of bed state and cleaner state.

FIG. 11 illustrates one embodiment of making assignments based on a combination of values of bed state and cleaner state. At 335, a cleaning request is received. In some embodiments, a cleaning request is automatically generated. The request may be based, for example, on one or more messages or indicators from an admission/discharge/transfer system. At 336, a value of a bed state for the request is determined. In one embodiment, possible values of a bed state include: Dirty; and Stat.

At 337, a value of a cleaner state is determined for one or more candidate cleaners. In one embodiment, possible values of a cleaner state include Free, On Break; Paged; In Progress; Paged to Stat; and In Progress on Stat. At 338, a determination is made of whether to assign a candidate based, at least in part, on the values of the bed state for the request and the value of the cleaner state for one or more of the candidate cleaners. In some embodiments, a cleaner is selected based at least in part on the suitability of the cleaner. For example, the cleaner may be selected based on having experience with the tasks required in the request. At 339, a cleaner is assigned to the cleaning request.

In some embodiments, a cleaner is immediately paged for a request. In certain embodiments, a page may be delayed for a specific amount of time or until one or more conditions are met. For example, a cleaner may be paged to perform one task when the cleaner notifies the system that he or she has completed a previously assigned task.

In certain embodiments, if a cleaner finishes the cleaner's current room, or if a cleaner comes back from break, or if a cleaner receives a new assignment, then the queue of requests is examined to see if any of the queued messages requesting services can be delivered.

Figure 12:
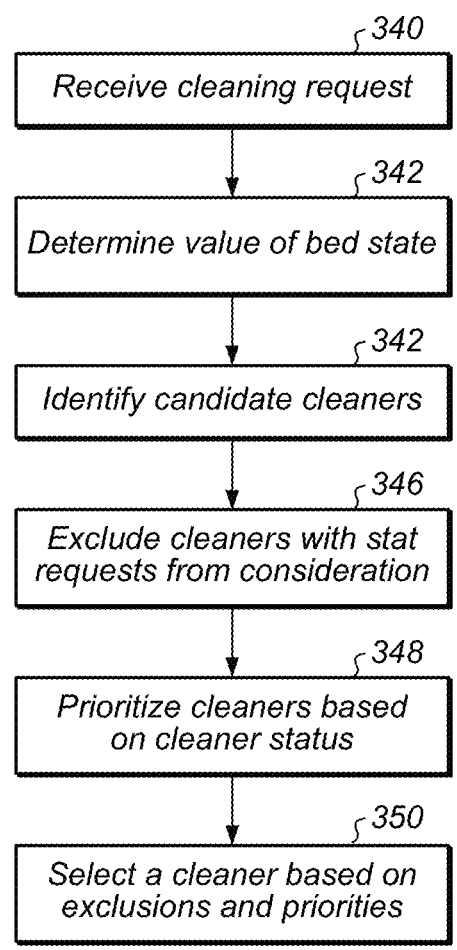
FIG. 12 illustrates one embodiment of managing cleaning services that excludes cleaners with uncompleted stat requests.

In some embodiments, cleaners with stat requests are excluded from consideration from other requests. FIG. 12 illustrates one embodiment of managing cleaning services that excludes cleaners with uncompleted stat requests. At 340, a cleaning request is received. At 342, a value is assessed for one or more beds in the request. In some embodiments, the possible values of bed state include a dirty state and a stat state.

At 344, a cleaner is selected for at least one of the requests from among two or more candidate cleaners. At 346, candidate cleaners are automatically excluded from consideration if the candidate cleaner has been paged for a prior stat request that is not yet completed; or is in progress on a prior stat request. At 348, candidate cleaners are prioritized based on cleaner status. In some embodiments, cleaners who are free have priority over cleaners who have been paged for a prior non-stat request that is not yet completed. Cleaners who are Free also have priority over cleaners who are in progress on a prior non-stat request. In some embodiments, cleaners are prioritized based on a suitability of the cleaners within the pool of candidates.

At 350, a cleaner is selected for the cleaning request. Selection of a cleaner may be based on exclusions for cleaners that have uncompleted stat requests, and on any prioritizations (such as prioritizations based on cleaner status).

Figure 13:
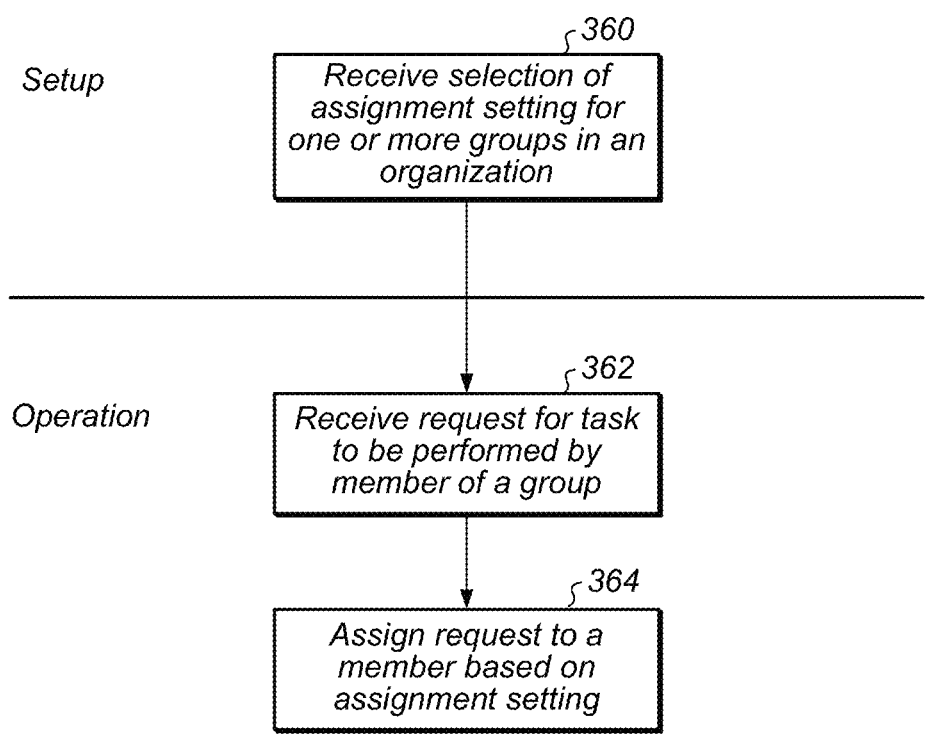
FIG. 13 illustrates one embodiment of assigning tasks based on a group assignment setting.

FIG. 13 illustrates one embodiment of assigning tasks based on a group assignment setting. At 360, a selection is received of an assignment setting for one or more groups or organizations. The setting may be established, for example, when a management system is initially placed into operation, during setup of the system, or at a later time. The assignment setting may be controlled by an administrator or by supervisory personnel at a health care facility. In one embodiment, a manager sets assignment codes for various units of the hospital to designate how tasks are to be assigned in each unit. In certain embodiments, assignment settings are set by each shift manager at the beginning of the shift.

In some embodiments, assignment settings for a group are defined by one or more codes. The codes may be entered in any manner, including keyboard entry, drop down menu, or any other means of entered a code choice. For example, a unit may be assigned "0" indicating that tasks are assigned manually (e.g., by the manager), a unit may be assigned "1" indicating that tasks are assigned to the designated cleaner for each particular task automatically (e.g., by the system), or a unit may be assigned "2" indicating that tasks are assigned to a cleaner automatically (e.g., by the system) based on availability (e.g., the cleaner that has been free for the longest time period).

Once the settings have been established, the system is operated to assign personnel to specific task requests, such as cleaning requests. At 362, a request is received for a task to be performed by a member of a group, such as the cleaning staff for a hospital unit. At 364, a member of the group is assigned based on the assignment setting. For example, in the example of codes given above relative to 360, if the code is set to 0, a manager may manually choose a cleaner for the assignment. If the code is set to 1, a cleaner may be assigned to the request automatically.

In certain embodiments, a cleaner is used in a reserve role. In one embodiment, a cleaner in a reserve role is assigned to a special zone having no beds. The cleaner may be available for the manager to manually dispatch assignments. A cleaner in a reserve role may not receive any automatic assignments from the system.

In some embodiments, a manager may assign one or more cleaners to a reserve role. In certain embodiments, all of the cleaners may be assigned to a reserve role. For example, on night shifts or other very low activity shifts, the manager may place all cleaners on reserve and dispatch all beds manually In one embodiment, cleaning assignments are cleared at the end of each manager's shift. After the assignments are cleared, the manager for the subsequent shift may assign tasks to cleaning personnel.

In various embodiments, a system automatically screens out, or adapts a response to, misleading messages. In one embodiment, messages generated by an ADT system are filtered to more accurately identify when bed cleaning requests are needed, thereby reducing, for example, premature requests for bed cleaning. A system may adapt a response in a manner that avoids wasting service resources (for example, a wasted trip to a room by cleaning personnel). In some embodiments, a system uses pattern matching to automatically detect misleading messages. For example, in cleaning management, the system may stop action from being taken to page cleaners or to change the states of bed unless a discharge or transfer that requires cleaning has actually occurred.

In various embodiments, messages coming into a system are assessed to determine whether they are misleading before personnel take action on the messages. In some embodiments, a service management system (such as an EVS management system) assesses messages fed from an ADT system. The system receiving the feed may determine whether the messages are misleading. An ADT message may be misleading, for example, if the message suggests that a patient is being discharged from a room when in fact the patient is not being discharged. For example, an HL7 message might indicate that a patient is being discharged, when in fact the patient is only undergoing a short procedure and will return to his or her room after the procedure.

In some embodiments, a system filters or adapts to messages indicating a "quick hop" scenario. In a "quick hop" scenario, a first message is received for the discharge of a first patient from a first bed, a second message is received for the admission of a second patient into the first bed previously occupied by the first patient, and due to a need to correct billing, misleading ADT messages are generated that indicate the second patient moving to another bed, the first patient being admitted into and discharged from the first bed, and the second patient being moved back into the first bed. The patients are not physically moved in response to the false messages, as the messages are merely entered into the system over a brief period of time (e.g., less than 5 min) to enable corrections in billing. If filtering of the messages is not applied, a cleaning request may be issued at each of the discharge messages, although cleaning may only be required when the patients are physically moved from the first bed (e.g., at the initial discharge of the first patient and the final discharge of the second patient). Similarly, in the context of intermediate transfers (e.g., transfers to Cardio Vascular Risk Assessments (CVRA) beds), a bed cleaning request may not be required as the patient is likely to return to their bed when an associated procedure is completed.

Figure 14:
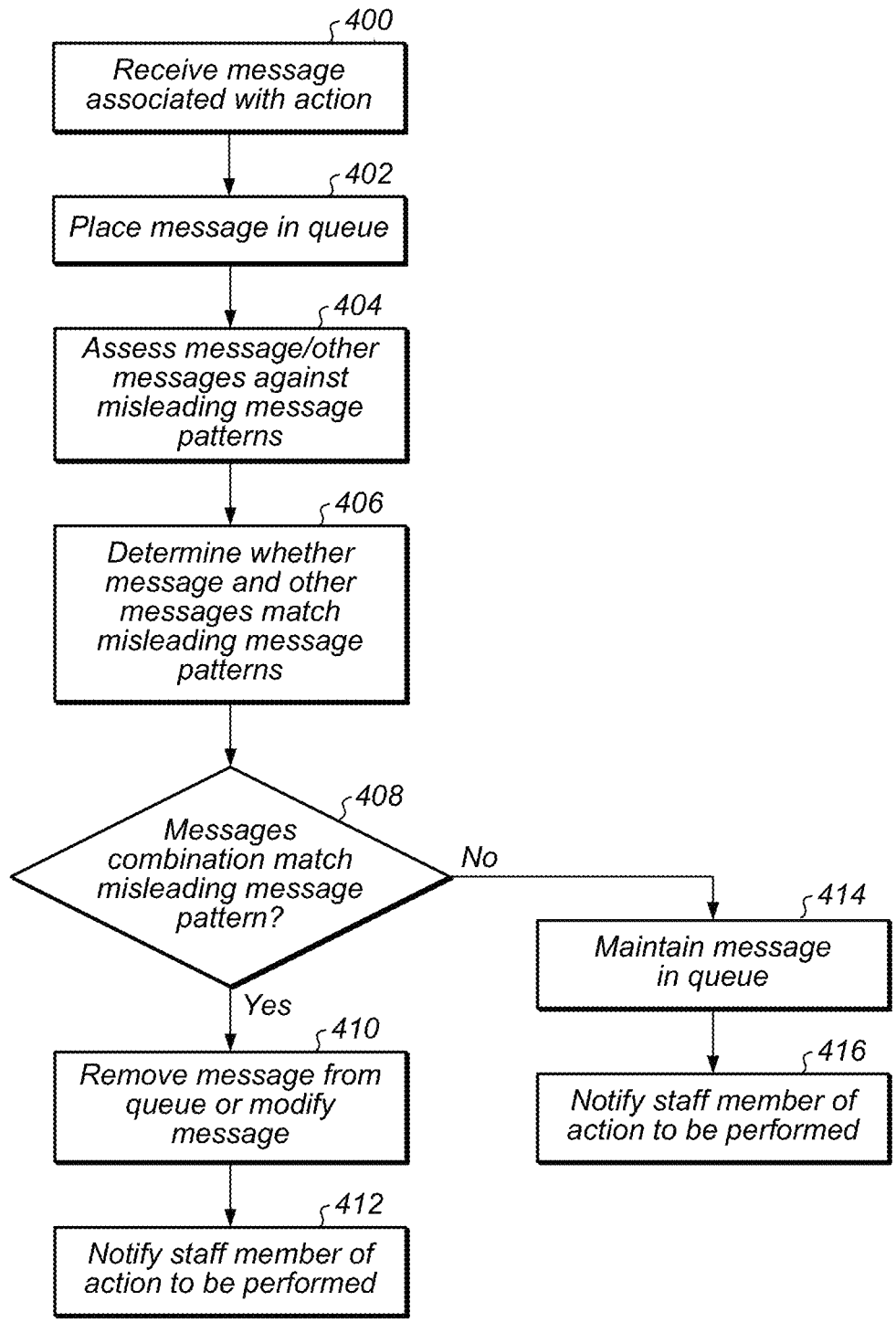
FIG. 14 illustrates one embodiment of managing services in a health care facility that includes detection of misleading messages.

FIG. 14 illustrates one embodiment of managing services in a health care facility that includes detection of misleading messages. At 400, one or more messages associated with actions to be performed in the health care facility are received. In some embodiments, the messages are HL7 messages. The messages may be initiated, for example, from an ADT system. In some embodiments, the message may be a call message. The call message may specify an action to be performed, such as a bed cleaning. Messages received may be assessed automatically, manually, or a combination thereof.

At 402, one or more of the messages are placed in a queue. At 404, a queued message is assessed, in combination with one or more other messages, against one or more misleading message patterns stored in a memory. Each of the misleading message patterns may reflect a different set of messages or characteristics of messages indicating or suggesting that a message is misleading. Examples of characteristics of messages or sets of messages include: the type of message; the time between receiving one type of message and another of message; or the sequence of messages (for example, a discharge message followed quickly by an admission message). A message or set of messages may be assessed against any number of misleading message patterns. Assessing messages and message sets may be performed sequentially, in parallel, or a combination of both.

At 406, a determination is made of whether the combination of the message and the one or more other messages matches one or more of the misleading message patterns. A pattern match may indicate or suggest that the message is misleading. At 408, each message combination is assessed for a match with misleading message patterns. If one or more of the misleading message patterns indicates or suggests that the message is misleading, the item may be removed from the queue or the message modified at 410. At 412, a staff member to be assigned the task may be notified that a task is to be performed and provided with a description of the task.

If none of the misleading message patterns indicates or suggests that a message is misleading, the message in the queue may be maintained in the queue at 414. At 416, one or more staff member may be notified and assigned an action to be performed in association with the message.

In some embodiments, a cleaning request is issued based on the type of ADT message received. For example, where an ADT message to discharge a patient is received, a cleaning request may be issued, as the discharge message may indicate a high likelihood of the need for a bed cleaning request. Where an ADT message is received for cancelling a discharge of a patient, however, a cleaning request may not be issued, as the cancellation of a discharge may be indicative of a high likelihood that the message and other related messages are false and, thus, no cleaning request need be issued. For example, where a cancel discharge message is received—placing the first patient back into the first bed—the preceding and following messages relating to movements of the first and second patients may be ignored such that no cleaning request is issued.

In some embodiments, issuing a cleaning request may be based on the destination of a patient. For example, where a message is received indicating movement of a patient from a first bed to a second bed associated with brief procedure, such as CVRA bed, it may be recognized that the patient is likely to return to the first bed, and a cleaning request for the first bed may not be issued at that time. Notably, however, if a subsequent message is received indicating movement of the patient from the first or second bed to another bed (e.g., which is associated with an extended stay) a cleaning request for the first bed and the second bed may be issued at that time.

In some embodiments, a delay is provided in the analysis of a request such that related ADT messages can be considered for the determination of whether or not to issue a corresponding bed cleaning request. For example, in the context of "quick hops", any billing corrections might be expected completed in a matter of 2-3 minutes. Accordingly, a 5 minute delay in processing messages and/or issuing a corresponding cleaning request may avoid issuing unneeded bed cleaning request based on false messages. For example, during the 5 minutes following the false message for the move of the second patient from the first to the second bed, a complete series of false messages request may be received, and processed to recognize no change in status (for example, the second patient remains in the first bed), such that no cleaning request is needed.

In some embodiments, managing services includes holding some or all of the messages received for a period of time. Messages on hold can be assessed, either alone or in combination with other messages, for characteristics that indicate or suggest that the messages are misleading messages. In some embodiments, held messages are assessed against misleading message patterns stored in the memory of a computer system. Held messages may be assessed automatically, manually, or a combination thereof.

Figure 15:
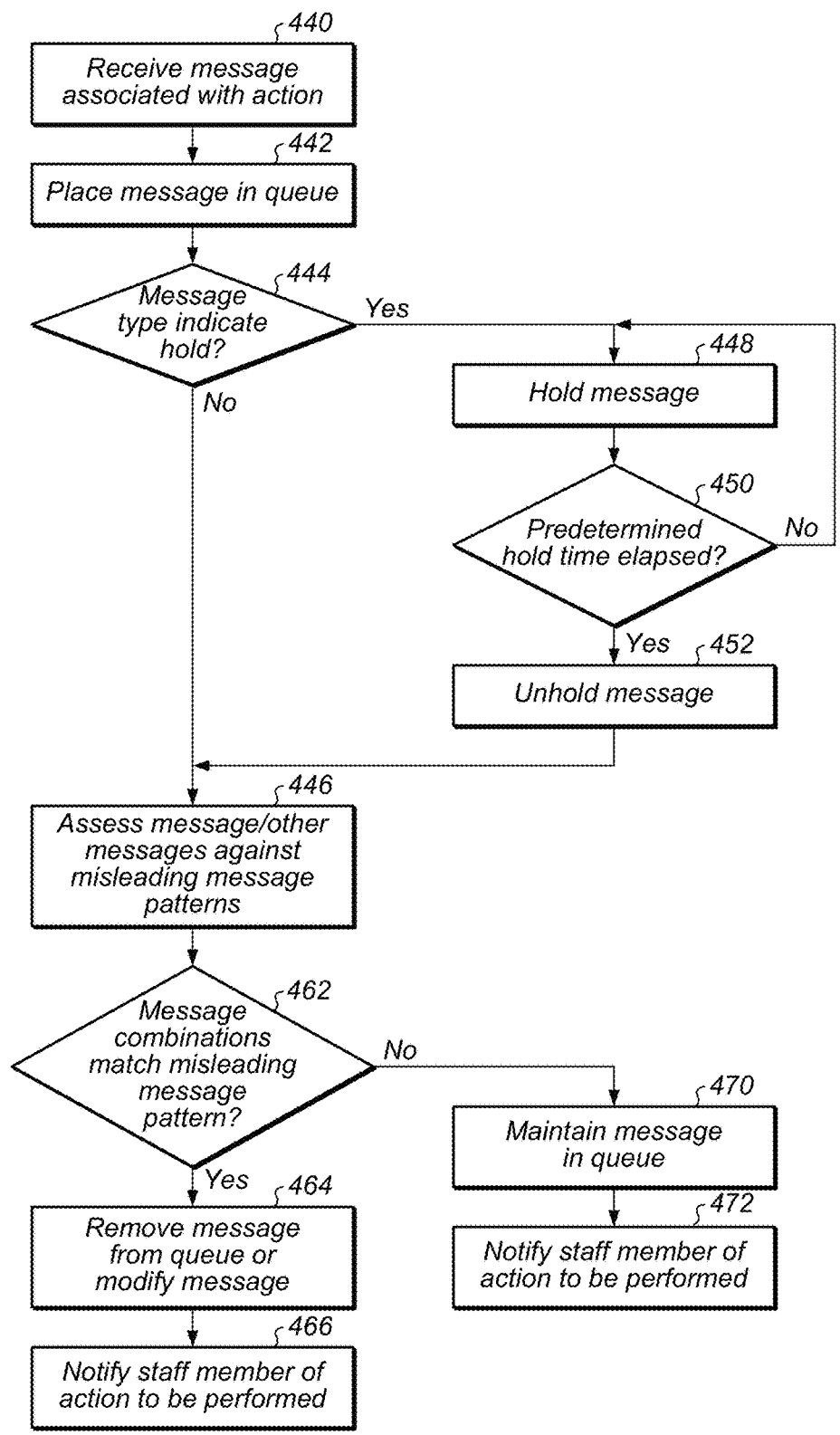
FIG. 15 illustrates one embodiment of managing services that includes holding and evaluating messages against misleading message patterns.

FIG. 15 illustrates one embodiment of managing services that includes holding and evaluating messages against patterns. At 440, one or more messages associated with one or more actions to be performed are received. At 442, messages are placed in a queue.

At 444, for one or more of the received messages, an assessment is made of based on one or more criteria to determine whether the message should be held. Criteria for determining whether a message should be held may include: characteristics of the message, such as the type of message (for example, admission, discharge, or transfer), characteristics of other messages, or the timing of the message relative to other messages.

One example of a message that may need to be held for assessment is a notification of a patient discharge. In many systems, a patient discharge message may immediately trigger a bed cleaning request. However, some patient discharge messages generated from an ADT system may be fictional messages that are later cancelled.

If the message is not of a type to be held, the message is processed in the queue at 446. If the received message should be held, a hold is applied to the message at 448. At 450, the message is tested as to whether a desired hold time has elapsed. The hold time for a message may be based on characteristics of the message, characteristics of other messages that appear to relate to the message, or the timing of the message relative to other messages. For example, the hold time for one type of message may be 30 seconds, while the hold time for another type of message may be 3 minutes. In some embodiments, the hold time can be modified by a user, such as a manager or administrator.

In certain embodiments, the hold time for a message is dynamically set. For example, the hold time for a message may change based on subsequent messages received from the system. For instance, a message may be released from hold based on the system receiving a subsequent message that validates the first message. As another example, the hold time for a message may be extended if a subsequent message raises the likelihood that the first message is misleading (increasing the suspicion level for the message).

Once the predetermined hold time has elapsed (or another condition has been met for releasing the hold), the message is unheld.

At 446, the unheld message is assessed, in combination with one or more other messages, against one or more misleading message patterns stored in a memory. At 462, a determination is made whether the combination of the unheld message and the one or more other messages matches one or more of the misleading message patterns. If one or more of the misleading message patterns indicates or suggests that the message is misleading, the message may be removed from the queue or modified at 464. At 466, a staff member (such as a bed cleaner) may be notified of the task and room location.

Modification of a message may include, for example, modifying timing of the task to be performed (such as delaying assignment or performance of the task) or the status of task (for example, stat or non-stat; complete or not complete). In certain embodiments, a staff member is notified of a cancellation or suspension of request for an action, such as a cleaning request previously assigned to the staff member.

If none of the misleading message patterns indicates or suggests that a message is misleading, the message may be maintained in the queue at 470. At 472, a staff member may be notified at least one staff member of at least one action to be performed in association with the message.

Figure 16:
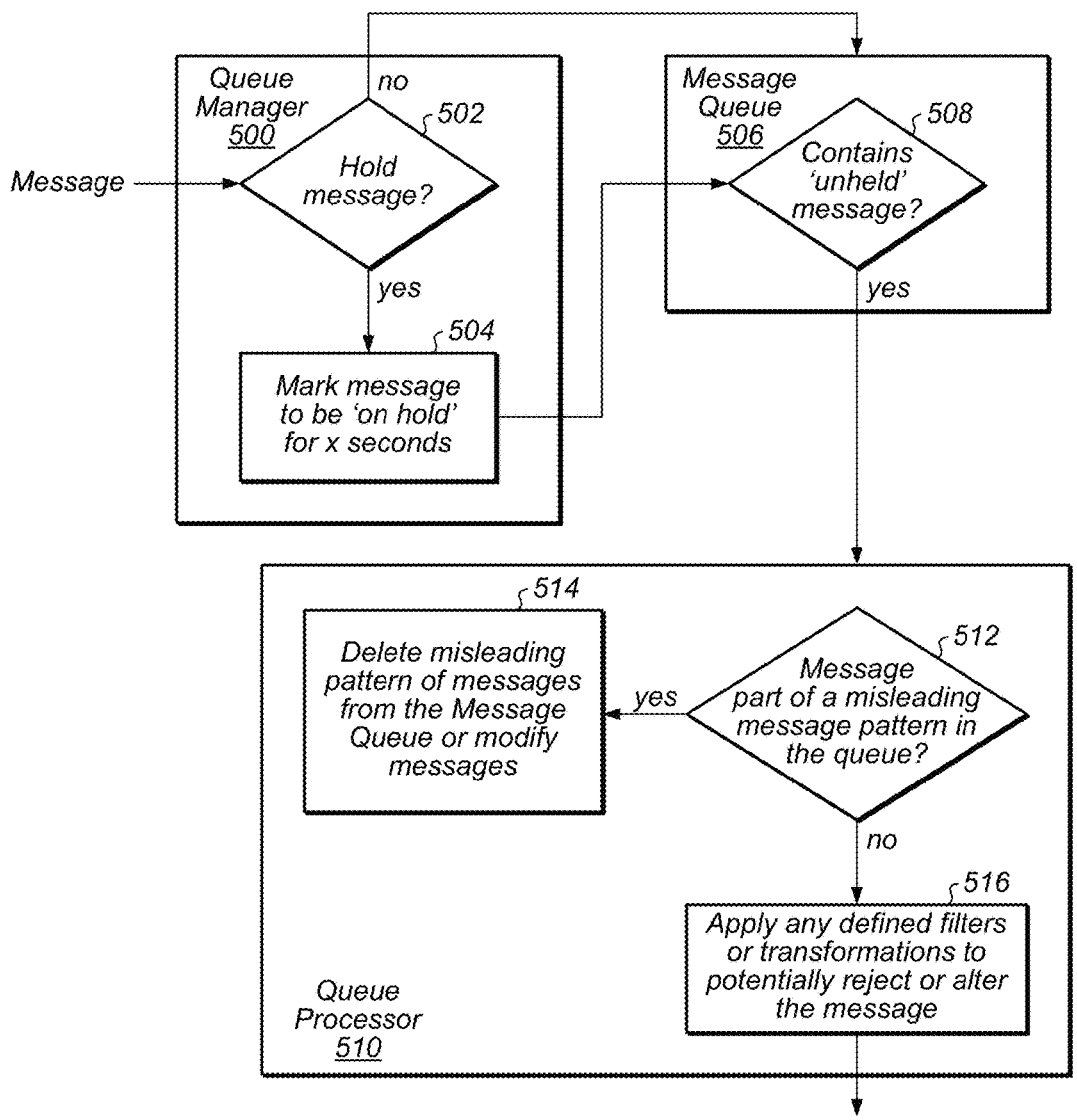
FIG. 16 is a flow diagram illustrating one embodiment of a delay pipeline for responding to service requests.

In some embodiments, a system implementing a delay pipeline detects and responds to misleading messages in a message feed used to trigger actions in a health care facility. FIG. 16 is a flow diagram illustrating one embodiment of a delay pipeline for responding to service requests.

A basic flow of a message through the delay pipeline may begin at message arrival at the Queue Manager program. In some embodiments, the message is an HL7 message. Queue Manager 500 may be responsible for determining if messages need to be put on hold. The messages may need to be put on hold, for example, if the messages may be later followed by a pattern of messages that indicates the initial message (and those following it that are part of the pattern) should be discarded. If it is determined a message should be put on hold at 502, Queue Manager 500 marks the message for a hold at 504 and indicates how long the message should be held in the Message Queue 506 before being processed. The message is then placed in Message Queue 506.

Each message is stored in Message Queue 506 until the message is no longer 'on hold' based on the elapsed time. At 508, when Message Queue 506 contains one or more unheld messages, Queue Processor 510 processes each message. The messages may be processed one at a time in the order they entered the queue in (for example, first in, first out). At 512, Queue Processor 510 looks at the current message and evaluates messages that are queued up after it to see if there is a match against one or more predefined misleading message patterns. If one of the misleading message patterns is identified, the system may remove from Queue Processor 510 some or all of the messages corresponding to the matched pattern at 514. The message may be deleted and discarded. If there are no matches with a misleading message pattern, the message may be processed by Queue Processor 510. Messages processed by Queue Processor 510 may have one or more custom filters or transformations applied as needed at 516 before continuing with processing of the message.

In some embodiments, Queue Manager 500 and Queue Processor 506 are part of a framework by which hold determination, misleading message detection, and filter/transformation logic are implemented. In one embodiment, hold determination, misleading message detection, and filter/transformation logic are implemented in a script written per-facility to define what logic is needed based on the facility the HL7 messages are coming from.

In some embodiments, when the amount of delay for messages has passed, the message is examined for the patterns and removed. If the message is not removed, then the message may be processed normally and sent to a bed board main system. A message may or may not trigger a notification to a staff member. For example, a bed moving from clean to occupied may not result in notification of any staff member, and may be considered a non-notifying event.

Different systems may generate different misleading messages and produce different misleading message patterns. In some embodiments, misleading message patterns are defined and stored for each of two or more different systems. For example, one set of misleading message patterns may be defined and installed on a system that will receive messages from an ADT system of type A, a different set of misleading message patterns may be defined and installed on a system that will receive messages from an ADT system of type B, and so on.

In some embodiments, a service management system, such as a bed cleaning management system, is used to manage services at two or more health care facilities. The system may receive messages from a message-generating system, such as ADT system, for each of the health care facilities. In some embodiments, the service management system is located in a cloud environment, such as described above relative to FIG. 2 and FIG. 3. For each different type of message generating system employed at the health care facilities, a different set of misleading message patterns may be installed into the memory of the service management system. During operation, as messages are received from each health care facility, the service management system may assess messages based on the set of patterns corresponding to the ADT system at the facility.

Transportation Dispatch System and Response

In some embodiments, transportation assignment notices are distributed over a network to a crowd of staff members. Staff members can offer/volunteer to take various assignments via the system. The system may automatically update assignment status based on staff member responses. Scores or similar performance measures can be posted to the crowd, to managers, or both.

In some embodiments, a system for providing services includes providing mobile devices to one or more candidate responders. In one embodiment, a system for providing transportation services in a health care facility includes a communication network, a transportation services management system, a dispatcher device, and one or more transport responder mobile devices. Elements of the system, such as dispatch devices and responder devices, may be distributed across various locations throughout a network. In one embodiment, a system for managing transportation services is as shown in FIG. 3. Transportation services management system may be provided on cloud 162. Mobile device 220 may be provided to a dispatch manager and serve as a dispatch device. Mobile devices 222 (at sites 202) and mobile devices 224 (at locations other than sites 202) may be provided to candidate transport responders and serve as transport responder mobile devices.

In various embodiments, dispatcher devices and transportation responder devices may exchange information relating to the transportation services jobs with one another and with a transportation services management system. Information on a dispatcher device may be displayed to a transportation dispatch manager. Information on a transportation responder device may be displayed to a transportation responder.

In some embodiments, a dispatcher device displays input screens for receiving transportation service requests into the system. Different input screens may be provided for different types of transportation requests. For example, one input screen may be provided to receive patient transportation requests, and another input screen may be provided to receive equipment transportation requests. FIG. 17 illustrates one embodiment of an input screen for receiving patient transportation requests. Patient transport request screen 600 includes hospital selection menu 602, transport type selection 604, transport specification window 606, requester information window 608, and destination window 610. A requester may make selections and enter information for transport requests in hospital selection menu 602, transport type selection 604, transport specification window 606, requester information window 608, and destination window 610. The requester may submit request by pressing the Submit Request button.

Figure 18:
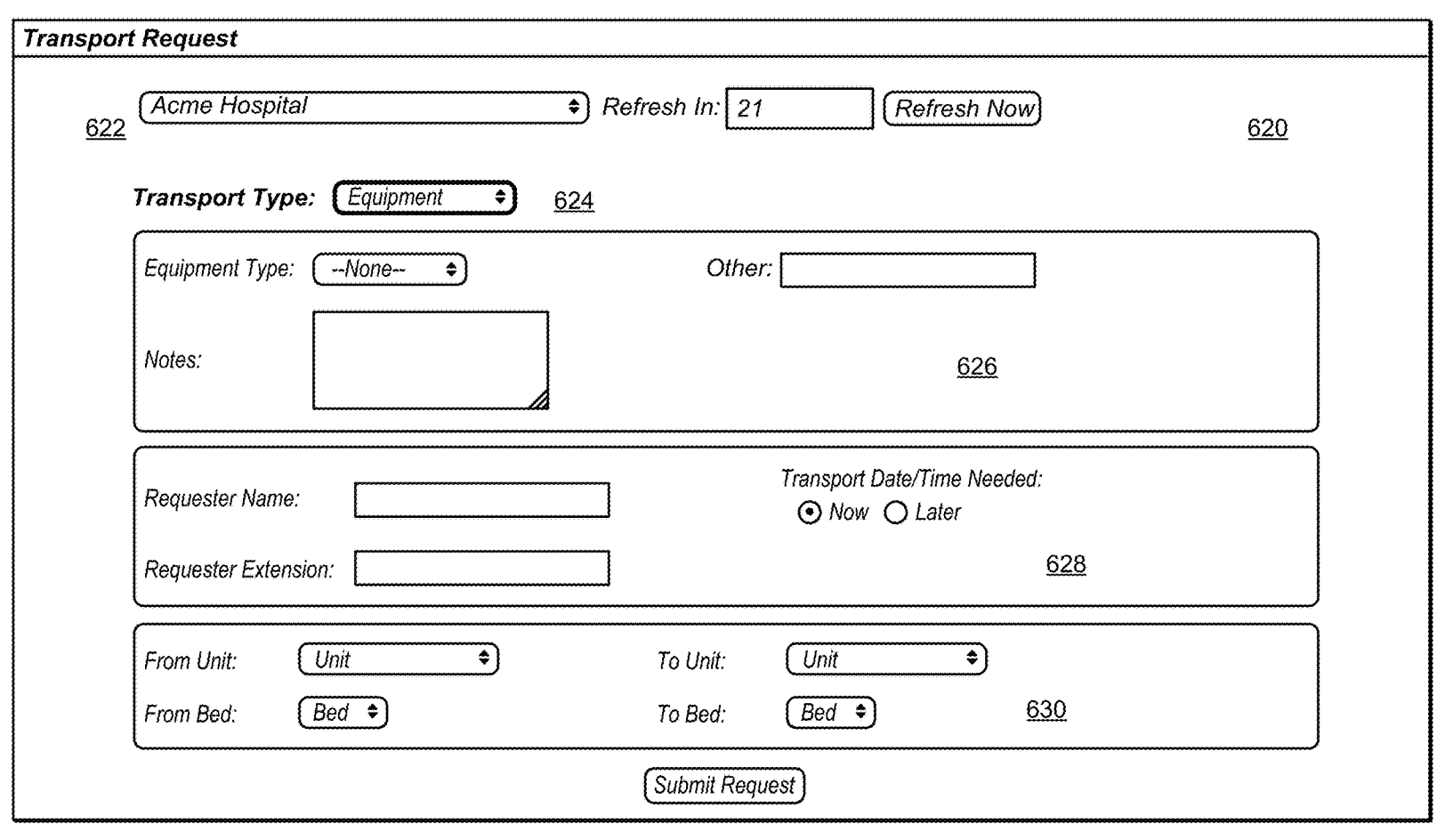

FIG. 18 illustrates one embodiment of an input screen for equipment transportation requests. Patient transport request screen 620 includes hospital selection menu 622, transport type selection 624, transport specification window 626, requester information window 628, and destination window 630. A requester may make selections and enter information for transport requests in hospital selection menu 622, transport type selection 624, transport specification window 626, requester information window 628, and destination window 630. The requester may submit request by pressing the Submit Request button.

FIG. 19 illustrates one embodiment of transportation assignments board display. Transportation assignments board 640 includes transporter list 642, pager list 644, and status list 646. Status list 646 may include information about transporters and the jobs they have been assigned to. A dispatcher may operate test pager button 648 to test any of the paging devices used by the transporters. In some embodiments, a manager can access a transporter list over a network to determine the status of every transporter at a glance.

In some embodiments, a device displays a transportation dispatch board. In one embodiment, the dispatch board simultaneously displays a request panel and a responder panel. The request panel may include a list of transportation service requests that need to be fulfilled. The responder panel may include a list of responders that are available to fulfill requests. The list may include information about each of the responders, such as responder status (for example, busy, off duty), what jobs they have been assigned, and qualifications. In some embodiments, a responder panel list is sorted in accordance with pre-determined criteria, such as availability, suitability, or both.

FIG. 20 illustrates one embodiment of a dispatch board for transport jobs. Dispatch board 660 includes request panel 662 and transporter panel 664. Request panel 662 includes information about specific requests, including state, destination, and assigned transporter. The display may include information about which transporters have been notified of the request, assigned to the request, or both. Transporter panel 664 includes status information for particular transporters, such as current job, pager device number, and status.

In some embodiments, a dispatch manager can initiate messages from an electronic dispatch board to transporters with mobile devices over a communication network. For example, from dispatch board 660 shown in FIG. 20, a dispatch manager may click on one of message icons 668 to create and send a message to any one of the transporters, no matter where the transported is located. The message may include any content (for example, the dispatch manager may enter the text of the message in a text box).

In some embodiments, a dispatch board allows a manager to send a message to all of the transporters on a network. The message may be sent to all of the transporters at once. For example, from dispatch board 660 shown in FIG. 20, a dispatch manager may click on one of radio tower icon 670 to create and send a message to any of the transporters no matter where the transporter is located.

Figure 21:
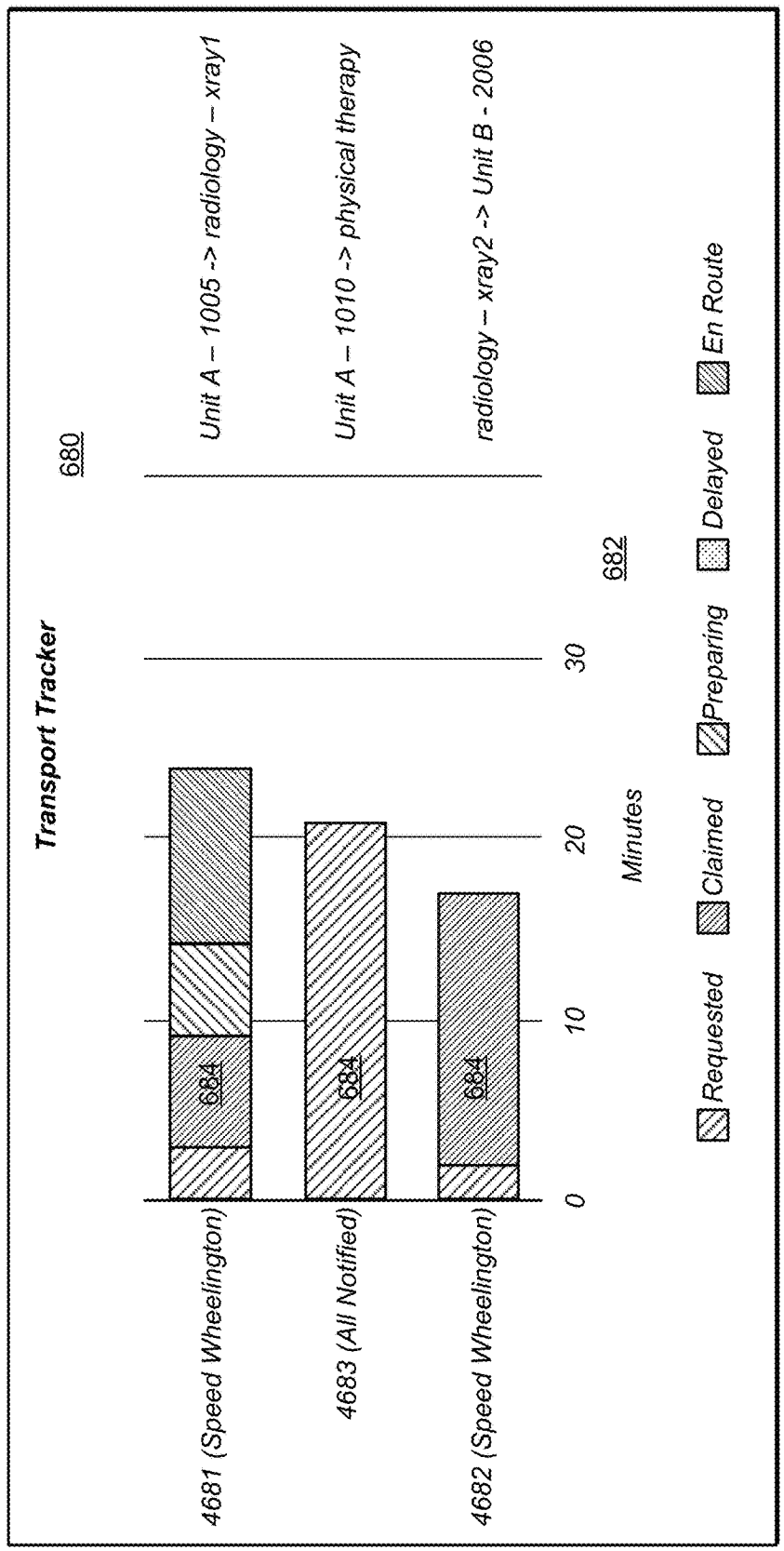
FIG. 21 illustrates one embodiment of a dispatch board for transport jobs.

In some embodiments, a system includes graphical representations of the status of service requests. In one embodiment, a graphical representation includes bars plotted against time. The bars may display responder progress for a particular job. FIG. 21 illustrates one embodiment of a dispatch board for transport jobs. Status display 680 includes timeline 682 and status bars 684. Status bars 684 display status and time-related information for different transport jobs. Each segment of a bar may correspond to a particular part of the life cycle of a task. In some embodiments, each segment of a status bar is a different color.

In some embodiments, a requester can view of each step in the progress of a request. For example, while sitting in the x-ray lab, the requester may check on the patient being delivered to the lab and get a great estimate of exactly how long until that patient will show up. In one embodiment, a requester tracks progress of a request by observing a timeline and/or status bars, such as timeline 682 and status bars 684 shown in FIG. 21.

FIG. 22 illustrates one embodiment of a rescheduler screen for transport requests. Rescheduler screen 700 includes destination window 702 and reschedule input window 704. A dispatcher may enter information in reschedule input window 704 to indicate a new need time and need date for a task.

FIG. 23 illustrates one embodiment of a patient return screen for transport requests. Patient return screen 720 includes original request window 722, new request window 724, and patient confirm ID entry field 726. A dispatcher may enter information or make menu selections to manage patient returns. For example, in the embodiment shown in FIG. 23, a dispatcher may request immediate return of a patient from the radiology xray1 location to a patient room.

FIG. 24 illustrates one embodiment of a status reporting screen for transportation services. Status reporting screen 740 includes transport type menu 742 and listing 744. In this example, transport type 742 selection is Patient Return. Listing 744 indicates the status of patient return requests.

Figure 25:
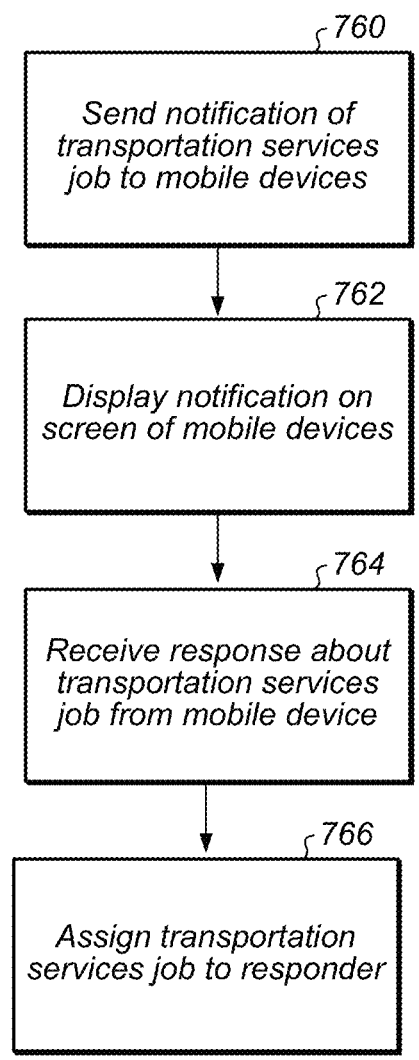
FIG. 25 illustrates one embodiment of transport dispatch with mobile devices.

FIG. 25 illustrates one embodiment of transport dispatch with mobile devices. At 760, a notification about a transportation services job is sent to a mobile device. The mobile device may be, for example, mobile device 112 described above relative to FIG. 1. At 762, the notification is displayed on a screen of the mobile device.

At 764, a response relating to the transportation services job may be received from the mobile device. The response may be an acceptance by a responder, a rejection by a responder, or other message.

At 766, the transportation services job is assigned to one or more responders. In some cases, the transportation services job is assigned to the responder that first transmitted acceptance of the job. In other cases, the transportation services job is assigned based on other criteria. In some embodiments, assignment or notification of assignment may be delayed, such as described above relative to FIGS. 14-16.

Figure 26:
FIG. 26 illustrates one embodiment of a display for job notification on a mobile device.

FIG. 26 illustrates one embodiment of a display for job notification on a mobile device. Notification screen 780 includes tabs 782 and jobs listing pane 784. Tabs 782 allow a user to toggle among the My Jobs, Unclaimed Jobs, and Transporter. In the example shown in FIG. 26, the user has selected the unclaimed jobs tab. Jobs 4683, 4681, and 4682 are displayed in list form. At this point, all of jobs 4683, 4681, and 4682 may be unclaimed. A transporter user may click on one of arrows 786 to display full details about any one of jobs 4683, 4681, and 4682. Unclaimed status indicators 786 indicate that none of jobs 4683, 4681, and 4682 have been claimed.

Tabs 782 allow a user to toggle among the My Jobs, Unclaimed Jobs, and Transporter. In the example shown in FIG. 26, the user has selected the unclaimed jobs tab. Jobs 4683, 4681, and 4682 are displayed in list form. At this point, all of jobs 4683, 4681, and 4682 may be unclaimed. A transporter user may click on one of arrows 786 to display full details about any one of jobs 4683, 4681, and 4682. Unclaimed status indicators 786 indicate that none of jobs 4683, 4681, and 4682 have been claimed.

In various embodiments, a system provides self-scheduling by transporters over communication network. For example, jobs are scheduled in advance by requesters. The due times may be spread over time (for example, over the course of a day). A transporter may use a mobile device to book the transporter's day and claim jobs from the job postings.

Figure 27:
FIG. 27 illustrates one embodiment of a display for job notification on a mobile device with user's claimed jobs.

FIG. 27 illustrates one embodiment of a display for job notification on a mobile device with user's claimed jobs. My Jobs tab may have been selected by the transporter user. Notification screen 780 has been updated to remove job 4683 from the listing, which may have been claimed by a transporter. A user transporter may click on 4681 to claim job 4681. Claimed indicator may be displayed for job 4681.

Figure 28:
FIG. 28 illustrates one embodiment of a job detail display on a mobile device for an unaccepted job.

FIG. 28 illustrates one embodiment of a job detail display on a mobile device for an unaccepted job. In this example, Job 4683 may as of yet be unclaimed. Details for Job 4683 are displayed in request information window 790.

Figure 29:
FIG. 29 illustrates one embodiment of a job detail display on a mobile device for an accepted job.

FIG. 29 illustrates one embodiment of a job detail display on a mobile device for an accepted job. In this example, Job 4683 has been selected. Details for Job 4683 are displayed in request information window 790. User may click to accept job 4683. Status indicator 792 may indicate that Job 4683 has been claimed. Status description 494 may indicate that the transporter is En Route to the location of the transportation request.

Figures 30, 31:
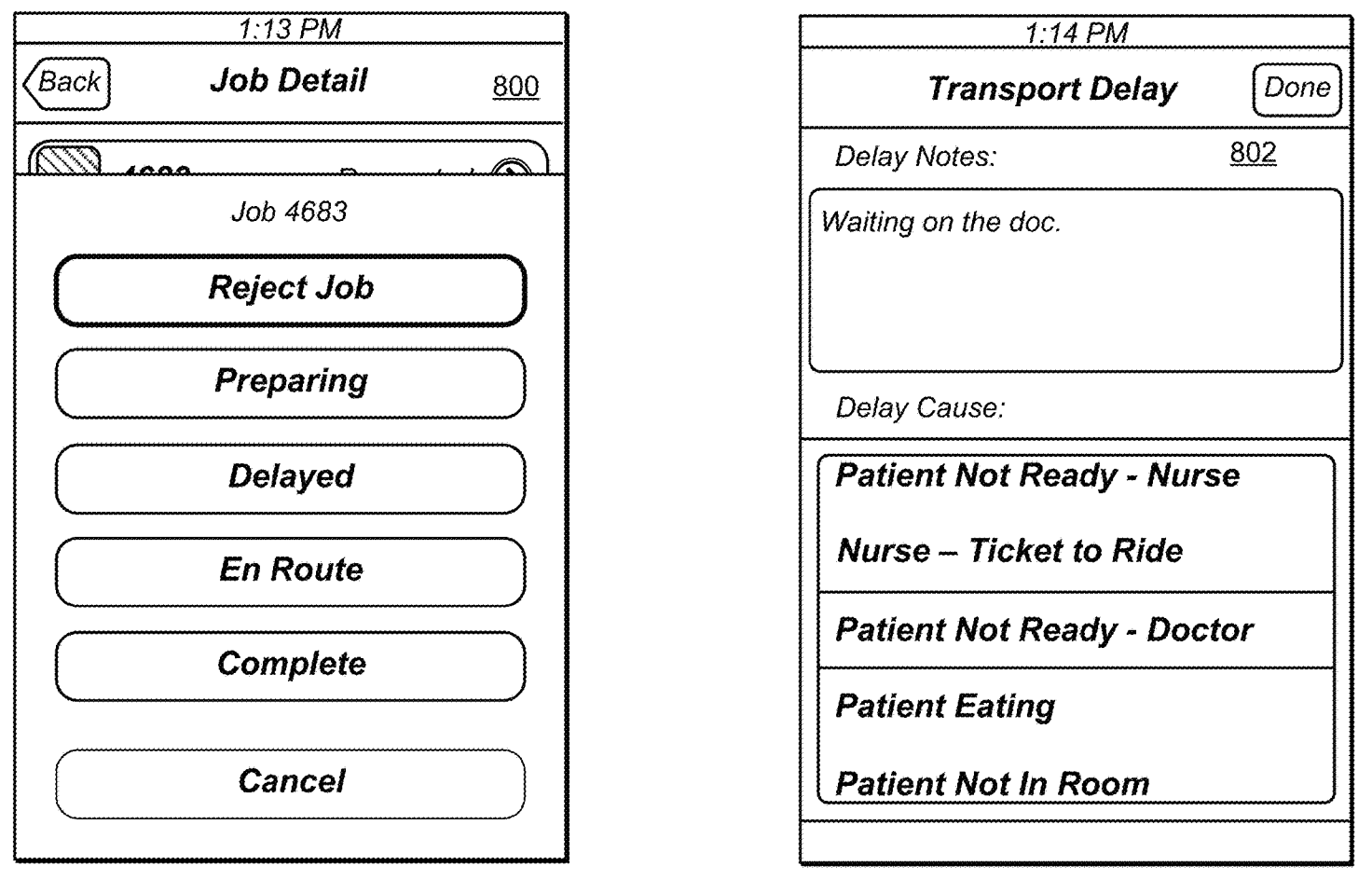

FIG. 30 illustrates a user menu for a making a selection on a job. Menu screen 800 presents options for Job 4683, including Reject Job, Preparing, Delayed, En Route, Complete, or Cancel. A transporter may select any one of the options by clicking on the appropriate button.

FIG. 31 illustrates a user menu for a screen for managing a transport delay over a mobile device. Screen 820 includes notes window 822 and delay cause window 824. A user may select one of the options in delay cause window 824. In some embodiments, a user may be prompted to update delay cause window at predetermined intervals.

In various embodiments, any of the screens described above relative to FIGS. 17-31 may be displayed on a mobile device, such as a smart phone. Some or all of the screens may, nevertheless in certain embodiments be displayed on other devices, such as a personal computer monitor or on a hospital electronic bulletin board.

In some embodiments, transportation services are provided using a crowd sourcing of responders with mobile devices. Crowd sourcing of responders may be used, in one embodiment, in response to a patient fall in a medical care facility. A system may apply rules for assigning responders from a group of responders based on pre-determined criteria.

Figure 32:
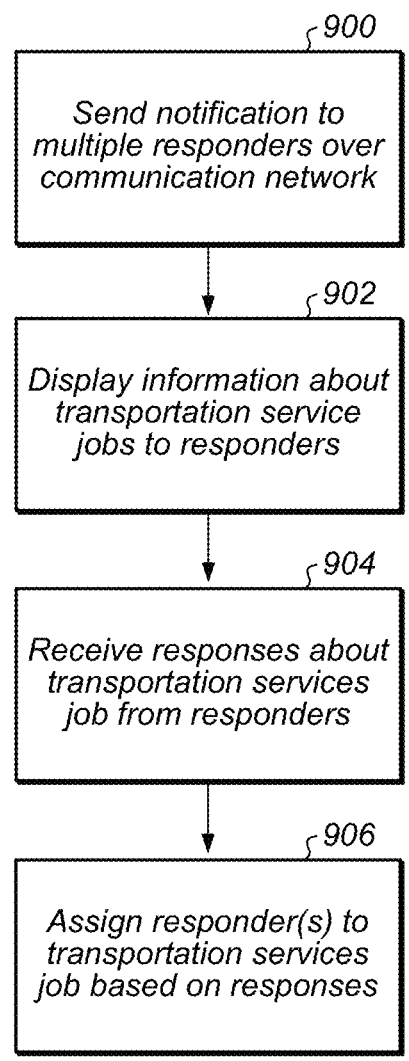
FIG. 32 illustrates an embodiment of providing transportation services that includes sending notifications to multiple responders over a communication network.

FIG. 32 illustrates an embodiment of providing transportation services that includes sending notifications to multiple responders over a communication network. At 900, a notification of a transportation services job is sent to two or more responders over a communication network. At 902, information about the transportation services job is displayed to the responders. Information about the transportation services job may be displayed to each responder, for example, over a mobile device, such as a smart phone.

At 904, a response relating to the transportation services job is received from one of the responders over receiving, over the network, from one or more of the responders. A responder may, for example, accept or reject the job.

At 906, one or more responders are assigned to the transportation services job based on the response to the job notification. A system may apply rules for assigning responders from a group of responders based on pre-determined criteria. In one embodiment, the system applies a predetermined cut-off number of responders. For example, the system may assign to responders to a job and then cut-off any further responders for the job. After the cut-off has been reached for a task, additional responders may be locked out of the task. In some embodiments, responders who were not selected may be notified that a task has been assigned to a different responder.

In some embodiments, a system allows messages to be exchanged between responders relating to transportation services job. For example, one responder may send a message to another responder that no additional help is needed for a patient fall, or that an additional piece of equipment is needed for a transportation services relating to the fall.

In some embodiments, a system may display status of one responder to other responders on the system. For example, the system may indicate: "Responder Katherine Post is en route to Room 1034," or "Responder Jacob Rusk has been delayed in responding to Job 4672".

In some embodiments, a system may display performance or responsiveness information about a responder to other responders. For example, the system may post that one responder has responded to three urgent requests in the last hour, or that another responder has not responded to any requests in the last 2 hours.

In some embodiments, measures of performance or responsiveness of responders is posted to some or all of the responders in an organization. The performance and responsive information may be posted over responder mobile devices. Performance posting may be refreshed as additional tasks are completed.

In some embodiments, a score is computed for each responder based on predetermined criteria. Examples of criteria that may be applied include:
- total number of jobs completed for a period
- average time to accept response
- average time to complete job
- rate of jobs completed
- distance traveled (for example, miles) to accomplish jobs
- ratings on difficulty of jobs
- peer performance ratings
- performance trends Scores for a responder may be calculated based on a formula that accounts for various factors in performance or the amount and quality of work completed. For example, completing a difficult task may results in a higher score than completing an easy task. Responders' scores may be updated over time as additional shifts are worked and additional tasks are completed.

Figure 33:
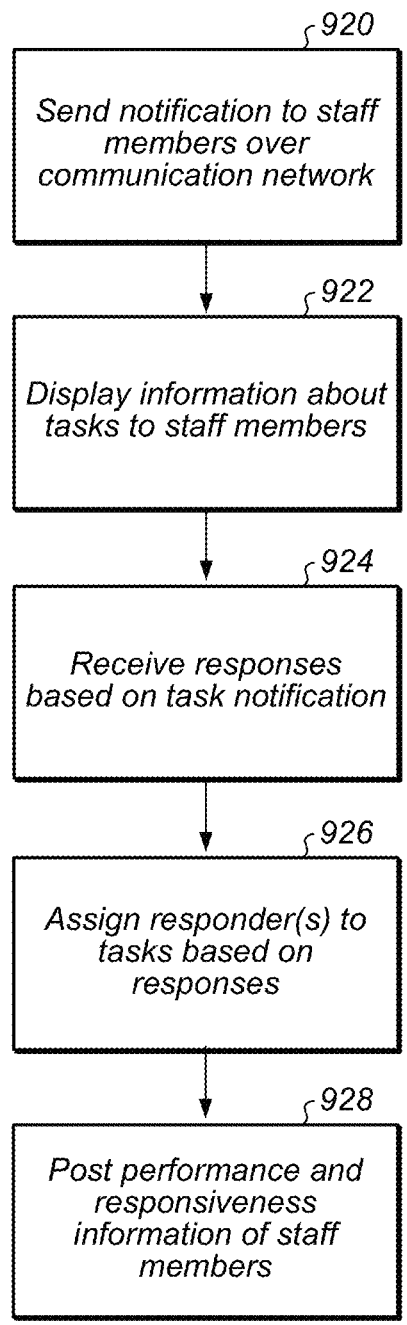
FIG. 33 illustrates one embodiment of managing the provision of services in a health care facility with posting of performance and responsiveness to staff members.

FIG. 33 illustrates one embodiment of managing the provision of services in a health care facility with posting of performance and responsiveness to staff members. At 920, a notification for one or more tasks is sent to staff members over a network. At 922, information about the tasks is displayed to the staff members.

At 924, a response relating to the tasks are received from one or more staff members. At 926, staff members are assigned to the tasks based on responses to the task notification.

At 928, performance and responsive information about the responders is posted to staff members over the network. Performance and responsiveness information may include the number of tasks completed by each responder, time to respond, and effectiveness of response. In some embodiments, performance and responsiveness information may include trends of responder, such as an increase in the rate of tasks completed relative to an earlier time period. For example, the posting may indicate that Jeff Philip's response count for the month has increased 30% from the previous month.

In some embodiments, staff members participate in a game or contest based on performance and responsive scores for responding to transportation services. In one example, all responders are ranked based on various aspects of the responder's performance, such as number of calls answered, total distance traveled. The responder with the highest score for a particular time period (for example, a day, a week, or a month) may be given an award or recognition. Awards may include special designations, prizes, bonuses, or other incentives. Implementing a game may promote competition among staff members to improve performance and responses.

FIG. 34 illustrates one a display board showing statistics and scores for a group of transporters according to one embodiment. In some embodiments, a performance/display board is posted on transporters' mobile devices. Board 940 includes transporter names 942, performance measures 944, and scores 946. Transporters may be sorted in order of scores 946 from highest to lowest. In this example, Speed Wheelington appears at the top of the listing based on a high level of response relative to the other transporters on the shift.

In some embodiments, a performance board may provide visibility to poor performer's among staff members. For example, board 940 provides information to the transporter staff that, during this shift, Sam Slover has only responded to one call and has spent substantially more time on break than the other transporters. Board 940 may be automatically updated as additional information concerning responses becomes available.

Computer systems may, in various embodiments, include components such as a CPU with an associated memory medium such as Compact Disc Read-Only Memory (CD-ROM). The memory medium may store program instructions for computer programs. The program instructions may be executable by the CPU. Computer systems may further include a display device such as monitor, an alphanumeric input device such as keyboard, and a directional input device such as mouse. Computer systems may be operable to execute the computer programs to implement computer-implemented systems and methods.

A computer system may allow access to users by way of any browser or operating system.

Computer systems may include a memory medium on which computer programs according to various embodiments may be stored. The term "memory medium" is intended to include an installation medium, e.g., Compact Disc Read Only Memories (CD-ROMs), a computer system memory such as Dynamic Random Access Memory (DRAM), Static Random Access Memory (SRAM), Extended Data Out Random Access Memory (EDO RAM), Double Data Rate Random Access Memory (DDR RAM), Rambus Random Access Memory (RAM), etc., or a non-volatile memory such as a magnetic media, e.g., a hard drive or optical storage. The memory medium may also include other types of memory or combinations thereof. In addition, the memory medium may be located in a first computer, which executes the programs or may be located in a second different computer, which connects to the first computer over a network. In the latter instance, the second computer may provide the program instructions to the first computer for execution. A computer system may take various forms such as a personal computer system, mainframe computer system, workstation, network appliance, Internet appliance, personal digital assistant ("PDA"), television system or other device. In general, the term "computer system" may refer to any device having a processor that executes instructions from a memory medium.

The memory medium may store a software program or programs operable to implement embodiments as described herein. The software program(s) may be implemented in various ways, including, but not limited to, procedure-based techniques, component-based techniques, and/or object-oriented techniques, among others. For example, the software programs may be implemented using ActiveX controls, C++ objects, JavaBeans, Microsoft Foundation Classes (MFC), browser-based applications (e.g., Java applets), traditional programs, or other technologies or methodologies, as desired. A CPU executing code and data from the memory medium may include a means for creating and executing the software program or programs according to the embodiments described herein.

Various embodiments may also include receiving or storing instructions and/or data implemented in accordance with the foregoing description upon a carrier medium. Suitable carrier media may include storage media or memory media such as magnetic or optical media, e.g., disk or CD-ROM, as well as signals such as electrical, electromagnetic, or digital signals, may be conveyed via a communication medium such as a network and/or a wireless link.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as embodiments. Elements and materials may be substituted for those illustrated and described herein, parts and processes may be reversed, and certain features of the invention may be utilized independently, all as would be apparent to one skilled in the art after having the benefit of this description of the invention. Methods may be implemented manually, in software, in hardware, or a combination thereof. The order of any method may be changed, and various elements may be added, reordered, combined, omitted, modified, etc. Changes may be made in the elements described herein without departing from the spirit and scope of the invention as described in the following claims.

What is claimed is:

1. A system for providing transportation services in a health care facility, comprising:
   a communication network;
   a transportation services management system configurable to store and retrieve information relating to dispatches of transportation services jobs at one or more health care facilities;
   one or more dispatcher devices, wherein each of at least one of the one or more dispatcher devices is configurable to:
      exchange with the transportation services management system, over the communication network, information relating to the transportation services jobs; and
      display information to a transportation dispatch manager; and
   two or more transport responder mobile devices, wherein each of at least one of the two or more transport responder mobile devices is configurable to:
      exchange with the transportation services management system, over the communication network, relating to the transportation services jobs; and
      display information to a transport responder,
   wherein the transportation services management system is configured to:
      send, to two or more candidate responders, via a plurality of the transport responder mobile devices, over the communication network, a notification about a transportation service job that needs to be performed;
      display, on at least two of the transport responder mobile devices, the notification;
      receive, by way of at least one of the transport responder mobile devices, a self-assignment to the transportation services job by at least one of the candidate responders;
      receive, by way of at least one other of the transport responder mobile devices, a response from each of at least one other of the candidate transport responders relating to the transportation services job;
      assign, by way of at least one of the transport responder mobile devices, based at least in part on the responses received from the at least one other transport responder mobile devices and pre-determined criteria for the number of responders for the transportation services job including a maximum cut-off, one or more additional candidate transport responders to perform the transportation services job; and
      notify, by way of at least one of the transport responder mobile devices, at least one other of the candidate responders that the transportation services job has been assigned to a different responder.

2. The system of claim 1, wherein the dispatch device is a mobile device.

3. The system of claim 1, wherein at least one of the dispatcher devices is configurable to display one or more input screens for receiving transportation service requests.

4. The system of claim 1, wherein at least one of the dispatcher devices is configurable to display one or more input screens for receiving transportation service requests, wherein at least a first one of the input screens is configurable to receive patient transportation requests, wherein at least a second one of the input screens is configurable to receive equipment transportation requests.

5. The system of claim 1, wherein the at least one of the dispatcher devices is configured to simultaneously display to a dispatcher:
   a request panel comprising a list of one or more transportation service requests; and
   a responder panel comprising a list of one or more responders.

6. The system of claim 5, wherein the transportation service request panel comprises a list of transportation service requests.

7. The system of claim 5, wherein responder panel is sorted based on one or more predetermined sorting criteria.

8. The system of claim 5, wherein the responder panel comprises availability information for at least one of the responders.

9. The system of claim 5, wherein the responder panel comprises suitability information for at least one of the responders.

10. The system of claim 1, wherein at least one of the dispatcher devices is configured to display all of the responders for a shift in a single list.

11. The system of claim 1, wherein at least one of the dispatcher devices is configured to receive a message entered by a dispatch manager and send the message to one of the responders.

12. The system of claim 1, wherein at least one of the dispatcher devices is configured to receive a message entered by a dispatch manager and send the message to all of the responders in an organization.

13. The system of claim 1, wherein the at least one of the dispatcher devices is configured to display, over a network, progress information for at least one transportation request to a requester of the request.

14. The system of claim 1, wherein assigning at least one of the candidate responders comprises applying, by the transportation services management system, one or more staffing rules for assigning responders to the transportation services job.

15. The system of claim 1, wherein the transportation services job is one of one or more transportation service jobs scheduled and posted in advance.

16. A tangible, non-transitory computer readable medium comprising program instructions stored thereon, wherein the program instructions are computer-executable to implement:
- sending, to two or more candidate responders, via a plurality of the transport responder mobile devices, a notification about a transportation services job that needs to be performed;
- displaying, on at least two of the transport responder mobile devices, the notification;
- receiving, by way of at least one of the transport responder mobile devices, a self-assignment to the transportation services job by at least one of the candidate responders;
- receiving, by way of at least one other of the transport responder mobile devices, a response from each of at least one other of the candidate transport responders relating to the transportation services job;
- assigning, by way of at least one of the transport responder mobile devices, based at least in part on the responses received from the at least one other transport responder mobile devices and pre-determined criteria for the number of responders for the transportation services job including a maximum cut-off, one or more additional candidate transport responders to perform the transportation services job; and
- notifying, by way of at least one of the transport responder mobile devices, at least one other of the candidate responders that the transportation services job has been assigned to a different responder.

* * * * *